(12) United States Patent
Wang et al.

(10) Patent No.: US 10,905,653 B2
(45) Date of Patent: Feb. 2, 2021

(54) SEQUENTIALLY DECOMPOSABLE POLYPEPTIDE-BASED NANOCARRIERS WITH PROTECTIVE SHELL AND PREPARATION THEREOF

(71) Applicant: National Tsing Hua University, Hsinchu (TW)

(72) Inventors: Li-Wen Wang, Hsinchu (TW); Tzu-Wei Wang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 679 days.

(21) Appl. No.: 15/331,460

(22) Filed: Oct. 21, 2016

(65) Prior Publication Data
US 2018/0078511 A1    Mar. 22, 2018

(30) Foreign Application Priority Data

Sep. 22, 2016 (TW) .............................. 105130644 A

(51) Int. Cl.
*A61K 9/14* (2006.01)
*A61K 9/51* (2006.01)
(Continued)

(52) U.S. Cl.
CPC .......... *A61K 9/5169* (2013.01); *A61K 9/0019* (2013.01); *A61K 9/146* (2013.01);
(Continued)

(58) Field of Classification Search
CPC ...... A61K 9/5169; A61K 9/141; A61K 9/143; A61K 9/146; A61K 9/4816; A61K 9/4825;
(Continued)

(56) References Cited

U.S. PATENT DOCUMENTS

| | | | | |
|---|---|---|---|---|
| 2011/0092416 | A1* | 4/2011 | Doyle | A61K 38/22 514/4.9 |
| 2014/0343340 | A1* | 11/2014 | Deshpande | C07C 1/20 585/639 |
| 2016/0334398 | A1* | 11/2016 | Weissleder | G01N 33/57449 |

OTHER PUBLICATIONS

Wang and Wang, Tailor Design Self-assembling and stimulus . . . , 2015 EWAB, of record (Year: 2015).*
(Continued)

*Primary Examiner* — Jeffrey E. Russel
(74) *Attorney, Agent, or Firm* — WPAT, PC

(57) ABSTRACT

Provided is a sequentially decomposable polypeptide-based nanocarrier with protective shell for delivery of hydrophobic drugs and preparation thereof. The nanocarrier includes a polypeptide-based long chain copolymer and a polypeptide-based short chain copolymer both assembling into an outer layer of hydrophilic polymer and a polypeptide core, wherein the polypeptide-based long chain copolymer includes a long-chain hydrophilic polymer and a first polypeptide chain; the polypeptide-based short chain copolymer includes a short-chain hydrophilic polymer and a second polypeptide chain; the first and the second polypeptide chains each sequentially includes an acidic amino acid segment, an acid-responsive amino acid segment, and a hydrophobic amino acid segment; the long-chain hydrophilic polymer is conjugated with the first polypeptide chain (Continued)

via an acid-labile linkage; an end of the short-chain hydrophilic polymer is conjugated with an active targeting molecule; and the polypeptide core includes a protective shell of an acid-soluble mineral on the acidic amino acid segment.

17 Claims, 15 Drawing Sheets

Specification includes a Sequence Listing.

(51) Int. Cl.
*A61K 47/42* (2017.01)
*A61K 9/00* (2006.01)
*A61K 31/427* (2006.01)
*A61K 31/704* (2006.01)
*A61K 38/05* (2006.01)

(52) U.S. Cl.
CPC .......... *A61K 9/5115* (2013.01); *A61K 9/5146* (2013.01); *A61K 31/427* (2013.01); *A61K 31/704* (2013.01); *A61K 38/05* (2013.01); *A61K 47/42* (2013.01); *Y10S 977/906* (2013.01)

(58) Field of Classification Search
CPC .......... A61K 9/50; A61K 9/51; A61K 9/5115; A61K 9/5146; A61K 47/02; A61K 47/30; A61K 47/32; A61K 47/34; A61K 47/42; Y10S 424/00; Y10S 514/00; Y10S 514/95; Y10S 977/906; Y10S 977/907
See application file for complete search history.

(56) References Cited

OTHER PUBLICATIONS

Sigma-Aldrich (downloaded Mar. 18, 2019 from https://www.sigmaaldrich.com/life-science/metabolomics/learning-center/amino-acid-reference-chart.html) (Year: 2019).*
Kim ( Calcium Carbonate-Mineralized Polymer Nanoparticles for pH-Responsive Robust Nanocarriers of Docetaxel, Macromolecular Research 2015, vol. 23, No. 1, pp. 111-117) (Year: 2015).*
Sens (Mixed Micelles in a Bidisperse Solution of Diblock Copolymers, Macromolecules 1996, 29: 4880-4890), (Year: 1996).*
Pelegri-O'Day (Therapeutic Protein-Polymer Conjugates: Advancing Beyond PEGylation, J. Am. Chem. Soc. 2014, 136: 14323-14332) (Year: 2014).*
Solaro (Targeted Delivery of Protein Drugs by Nanocarriers, Materials 2010, 3: 1928-1980) (Year: 2010).*
Grover (Protein-Polymer Conjugates: Synthetic Approaches by Controlled Radical Polymerizations & Interesting Applications, Curr Opin Chem Biol. 2010, 14: 818-827) (Year: 2010).*
Frand (p. 203, 1st para, Pathways for protein disulphide bond formation, Trends in Cell Biology 2000, 10:203-210) (Year: 2000).*
Li-Wen Wang et al., Tailor Design Self-assembling and Stimulus-Responsive Polypeptide-based Nanoparticles or Active Targeted Drug Delivery, East West Asia Biomaterials Symposium, Oct. 21, 2015, p. 23, Antalya, Turkey.
Li-Wen Wang et al., Tailor Design Self-assembling and Stimulus-Responsive Polypeptide-based Nanoparticles for Active Targeted Drug Delivery, 21st International Biomedical Science and Technology Symposium, Oct. 22-Oct. 24, 2015, p. 180, Antalya, Turkey.

* cited by examiner

US 10,905,653 B2

SEQUENTIALLY DECOMPOSABLE POLYPEPTIDE-BASED NANOCARRIERS WITH PROTECTIVE SHELL AND PREPARATION THEREOF

CROSS-REFERENCE TO RELATED APPLICATION

This application claims priority of Taiwan patent application No. 105130644, filed on Sep. 22, 2016, the content of which is incorporated herein in its entirety by reference.

BACKGROUND OF THE INVENTION

1. Field of the Invention

The present invention relates to nanocarriers for drug delivery. Particularly, the present invention relates to sequentially decomposable polypeptide-based nanocarriers with protective shell and preparation thereof.

2. The Prior Art

In recent years, research in nanotechnology has been largely focusing on development of nanocarriers as a platform for drug delivery in the body in order to treat or diagnose diseases, especially for delivery of anti-cancer drug. The goals of nanocarrier development include increase of safety and biocompatibility, drug delivery with high specificity, high drug loading efficiency and high drug release, and high stability of nanocarriers. By stable encapsulation of drugs in nanocarriers during drug delivery and complete drug release into target cells, the effective concentrations of drugs acting on target cells would be elevated and the toxic side effects to normal tissues would be reduced. However, it is difficult for the currently known nanocarriers to possess all the advantages mentioned above because of the limited materials and designs.

For example, liposomes, which are composed of lipids, have become the dominant carriers of anti-cancer drugs in the current market due to their good biocompatibility and biodegradability. However, they possess poor structural stability in the blood. Drug leakage from liposomes during the delivery process causes side effects, including nausea, vomiting, loss of appetite, and hair loss. Though it has been reported that surface modifications of nanocarriers with polyethylene glycol (PEG) may decrease their clearance from blood by the mononuclear phagocytic system, elongate their circulation half-time in blood, and improve their stability, lower uptake of liposomes with PEG modification by cells has been observed. Even if the PEG-modified liposomes are taken up by target cells, a lack of mechanisms for accelerated drug release from liposomes leads to incomplete release of drugs and thus the lowered effective concentration.

Furthermore, one of the strategies to increase specificities of nanocarriers to target cells is to conjugate active targeting molecules, such as monoclonal antibodies, aptamers, peptides, and small molecules, to the surfaces of nanocarriers, so that the active targeting molecules would bind to specific receptors on target cell surfaces and direct the nanocarriers to the target cells. Yet, the exposed active targeting molecules also bind to surface molecules of non-target cells, which leads to drug delivery to non-target cells and causes toxic side effects.

SUMMARY OF THE INVENTION

In one aspect, the present invention provides a sequentially decomposable polypeptide-based nanocarrier with protective shell, comprising a plurality of polypeptide-based long chain copolymers and a plurality of polypeptide-based short chain copolymers both assembling into an outer layer of hydrophilic polymer and a polypeptide core, wherein the polypeptide core comprises a protective shell and a decomposition accelerating layer from the outside to the inside, wherein the polypeptide-based long chain copolymers and the polypeptide-based short chain copolymers are aligned along long axes thereof and interspersed in the polypeptide-based nanocarrier with protective shell, wherein the polypeptide-based long chain copolymer comprises a long-chain hydrophilic polymer and a first polypeptide chain from the outer layer of hydrophilic polymer to the polypeptide core, and the polypeptide-based short chain copolymer comprises a short-chain hydrophilic polymer and a second polypeptide chain from the outer layer of hydrophilic polymer to the polypeptide core; the first polypeptide chain and the second polypeptide chain each sequentially comprises an acidic amino acid segment, an acid-responsive amino acid segment, and a hydrophobic amino acid segment from near the outer layer of hydrophilic polymer, and the first polypeptide chain and the second polypeptide chain have the same amino acid sequence; the long-chain hydrophilic polymer and the acidic amino acid segment of the first polypeptide chain are conjugated by an acid-labile linkage, and an end of the short-chain hydrophilic polymer far from the polypeptide core is conjugated with an active targeting molecule; the protective shell of the polypeptide core is an acid-soluble mineralized protective shell comprising an acid-soluble mineral deposited on the acidic amino acid segment, and the decomposition accelerating layer consists essentially of the acid-responsive amino acid segment.

In another aspect, the present invention provides a sequentially decomposable polypeptide-based nanocarrier with protective shell, comprising a plurality of polypeptide-based long chain copolymers and a plurality of polypeptide-based short chain copolymers both assembling into an outer layer of hydrophilic polymer and a polypeptide core, wherein the polypeptide core comprises a protective shell and a decomposition accelerating layer from the outside to the inside, wherein the polypeptide-based long chain copolymers and the polypeptide-based short chain copolymers are aligned along long axes thereof and interspersed in the polypeptide-based nanocarrier with protective shell, wherein the polypeptide-based long chain copolymer comprises a long-chain hydrophilic polymer and a first polypeptide chain from the outer layer of hydrophilic polymer to the polypeptide core, and the polypeptide-based short chain copolymer comprises a short-chain hydrophilic polymer and a second polypeptide chain from the outer layer of hydrophilic polymer to the polypeptide core; the first polypeptide chain and the second polypeptide chain each sequentially comprises a cysteine segment, an acid-responsive amino acid segment, and a hydrophobic amino acid segment from near the outer layer of hydrophilic polymer, and the first polypeptide chain and the second polypeptide chain have the same amino acid sequence; the long-chain hydrophilic polymer and the cysteine segment of the first polypeptide chain are conjugated by an acid-labile linkage, and an end of the short-chain hydrophilic polymer far from the polypeptide core is conjugated with an active targeting molecule; the protective shell of the polypeptide core is a redox-responsive protective shell comprising a plurality of disulfide bonds between the cysteine segments of the polypeptide-based long chain copolymers and the polypeptide-based short chain copolymers in proximity to each other, and the decomposition accelerating layer consists essentially of the acid-responsive amino acid segment.

In one embodiment of the present invention, the polypeptide-based long chain copolymers and the polypeptide-based short chain copolymers are in a molar ratio of about 1:2 to 2:1, and the polypeptide-based nanocarrier with protective shell is at a size of about 100-200 nm.

In another embodiment of the present invention, the acidic amino acid segment consists of 10-20 acidic amino acid residues, the acid-responsive amino acid segment consists of 5-15 acid-responsive amino acid residues, and the hydrophobic amino acid segment consists of 5-15 hydrophobic amino acid residues; the acid-responsive amino acid segment consists of an amino acid having a side chain with a pKa value of about 6, such as histidine; the acidic amino acid segment consists of glutamic acid, aspartic acid, or combinations thereof.

In another embodiment of the present invention, the acid-labile linkage is a linkage hydrolyzed at pH 6.5-7, such as a cis-aconityl linkage provided by aconitic anhydride.

In yet another embodiment of the present invention, the acid-soluble mineral is calcium phosphate or calcium carbonate.

In still another embodiment of the present invention, the sequentially decomposable polypeptide-based nanocarrier with protective shell further encapsulates a hydrophobic agent, such as the anti-cancer drug doxorubicin that intercalates DNA, angiogenesis inhibitors, and inhibitors of metastasis.

In one further aspect, the present invention provides a method of preparing the sequentially decomposable polypeptide-based nanocarrier with protective shell previously described, comprising the steps of: (a) preparing separately a polypeptide-based long chain copolymer and a polypeptide-based short chain copolymer by chemical grafting, wherein the polypeptide-based long chain copolymer comprises a long-chain hydrophilic polymer and a first polypeptide chain, and the polypeptide-based short chain copolymer comprises a short-chain hydrophilic polymer and a second polypeptide chain; the first polypeptide chain and the second polypeptide chain each sequentially comprises an acidic amino acid segment, an acid-responsive amino acid segment, and a hydrophobic amino acid segment, and the first polypeptide chain and the second polypeptide chain have the same amino acid sequence; the long-chain hydrophilic polymer and the acidic amino acid segment of the first polypeptide chain are conjugated by an acid-labile linkage, and an end of the short-chain hydrophilic polymer is conjugated with an active targeting molecule, (b) mixing the polypeptide-based long chain copolymer and the polypeptide-based short chain copolymer in a polar solvent to allow self-assembly into a polypeptide-based nanocarrier, and (c) adding a cation aqueous solution and an anion aqueous solution into the polar solvent containing the polypeptide-based nanocarrier to form a first layer of an acid-soluble mineralized protective shell on the acidic amino acid segment of the polypeptide-based nanocarrier, and repeating the addition step multiple times for formation of multiple layers of the acid-soluble mineralized protective shell to obtain the polypeptide-based nanocarrier with protective shell.

For the method of the present invention, in step (a) the acidic amino acid segment consists of 10-20 acidic amino acid residues, the acid-responsive amino acid segment consists of 5-15 acid-responsive amino acid residues, and the hydrophobic amino acid segment consists of 5-15 hydrophobic amino acid residues; the acid-responsive amino acid segment consists of an amino acid having a side chain with a pKa value of about 6, such as histidine; the acidic amino acid segment consists of glutamic acid, aspartic acid, or combinations thereof; the acid-labile linkage is hydrolyzed at pH 6.5-7; in step (b) the polypeptide-based long chain copolymer and the polypeptide-based short chain copolymer are mixed in a molar ratio of about 1:2 to 2:1; in step (c) the cation aqueous solution is a calcium ion aqueous solution, the anion aqueous solution is a phosphate aqueous solution or carbonate aqueous solution, and the addition step is repeated at least 5 times.

The sequentially decomposable polypeptide-based nanocarrier with protective shell is of low toxicity to living cells and is safe to use because it is made of materials that are biocompatible and biodegradable.

For the sequentially decomposable polypeptide-based nanocarrier with protective shell of the present invention, it is characterized that its structure varies according to the environment. At the physiological condition of pH 7.4, for example, in the blood stream, the polypeptide-based nanocarrier with protective shell exists intact in a compact and stable structure. However, when it is in an acidic environment with a pH value lower than 7, for example, in tumor tissues or in the endosome-lysosome system in cell, its structure gradually collapse in response to lowered pH values. Thus, the sequentially decomposable polypeptide-based nanocarrier with protective shell of the present invention displays pH responsiveness and achieves the goal of sequential decomposition based on pH change by using the following designs: (1) the acid-labile linkage between the long-chain hydrophilic polymer and the first polypeptide chain in the polypeptide-based long chain copolymer; (2) the acid-soluble mineralized protective shell formed on the acidic amino acid segments of both the polypeptide-based long chain copolymers and the polypeptide-based short chain copolymers; (3) the acid-responsive amino acid segments in both the polypeptide-based long chain copolymers and the polypeptide-based short chain copolymers. Also, the sequentially decomposable polypeptide-based nanocarrier with protective shell of the present invention may achieve the goal of sequential decomposition upon changes in both pH values and redox status of the environment by otherwise having a redox-responsive protecting shell.

One advantage of applying the sequentially decomposable polypeptide-based nanocarrier with protective shell of the present invention in drug delivery is the increased structural stability, which prevents instant decomposition of the nanocarrier upon injection into the body, elongates the circulation time of the nanocarrier in the blood stream while maintaining its impact structure, and thus avoids drug leakage from the nanocarrier before reaching the target site. This advantage comes mainly from the protective shell of the polypeptide-based nanocarrier with protective shell of the present invention. The protective shell either exists as an acid-soluble mineralized protective shell, which is formed from deposition of acid-soluble minerals on the acidic amino acid segments of both the polypeptide-based long chain copolymers and the polypeptide-based short chain copolymers because of the negative charges carried by those acidic amino acid segments, or exists as a redox-responsive protective shell, which is formed from disulfide bonds between the cysteine segments of both the polypeptide-based long chain copolymers and the polypeptide-based short chain copolymers in proximity to each other. Besides, for complete release of the encapsulated drugs into the target cells of tumor tissues, the polypeptide-based nanocarrier with protective shell of present invention possesses the multi-pH responsiveness and the redox responsiveness due to the previously described designs to achieve the goals of sequential decomposition of the nanocarrier and accelerated drug release.

In addition, the polypeptide-based nanocarrier with protective shell of present invention conjugates an active targeting molecule to the end of the short-chain hydrophilic polymer of the polypeptide-based short chain copolymer to promote uptake of the nanocarrier by the target cells of tumor tissues. For prevention of nonspecific binding of the active targeting molecules to non-target cells, the polypeptide-based nanocarrier with protective shell of the preset invention buries the active targeting molecules in the long-chain hydrophilic polymers of the polypeptide-based long chain copolymers. It is only when the nanocarrier reaches the tumor tissue at a slightly acidic pH that the active targeting molecules of the polypeptide-based short chain copolymers would be exposed and recognized by target cells as a result of breakage of the acid-labile linkage and detachment of the long-chain hydrophilic polymers from the remaining part of the polypeptide-based long chain copolymers. In this way, the active targeting molecules are protected from the nonspecific binding to non-target cells, which leads to prevention of toxic side effects caused by delivery of drugs to the non-target cells. Furthermore, detachment of the long-chain hydrophilic polymers from the remaining part of the polypeptide-based long chain copolymers allows the polypeptide-based nanocarrier with protective shell of the present invention to be taken up by target cells more easily.

The present invention is further explained in the following drawings and examples. It is understood that the examples given below do not, however, limit the scope of the invention, and it will be evident to those skilled in the art that modifications can be made without departing from the scope of the appended claims.

BRIEF DESCRIPTION OF THE DRAWINGS

FIGS. 6A-6B are images of the nanocarriers at pH 7.4; FIGS. 6C-6F are images of the nanocarriers at pH 5.0 for 20 minutes, 40 minutes, 1 hour, and about 4 hours, respectively; the scale bars in FIGS. 6A, 6C, and 6D represent 0.5 µm; the scale bars in FIG. 6B represents 100 nm; the scale bars in FIGS. 6E-6F represent 1 µm;

DETAILED DESCRIPTION OF THE PREFERRED EMBODIMENT

The present invention provides a sequentially decomposable polypeptide-based nanocarrier with protective shell and preparation thereof. In the first part of following examples, the amphiphilic molecules of the polypeptide-based long chain copolymer and the polypeptide-based short chain copolymer were separately prepared by chemical grafting. The polypeptide-based long chain copolymer comprises a long-chain hydrophilic polymer and a first polypeptide chain, and the polypeptide-based short chain copolymer comprises a short-chain hydrophilic polymer and a second polypeptide chain. Each of the first polypeptide chain and the second polypeptide chain sequentially comprises an acidic amino acid segment, an acid-responsive amino acid segment, and a hydrophobic amino acid segment, and the first polypeptide chain and the second polypeptide chain have the same amino acid sequence. Besides, the polypeptide-based long chain copolymer comprises an acid-labile linkage such as a cis-aconityl linkage, which is hydrolyzed at pH 6.5-7, conjugating the long-chain hydrophilic polymer to the acidic amino acid segment of the first polypeptide chain. The polypeptide-based short chain copolymer comprises an active targeting molecule, for example, the LyP-1 peptide, conjugated with the end of the short-chain hydrophilic polymer.

Next, the polypeptide-based long chain copolymer, the polypeptide-based short chain copolymer, and a hydrophobic drug were mixed in a polar solvent to allow self-assembly into a drug-loaded polypeptide-based nanocarrier with an outer layer of hydrophilic polymer and a polypeptide core. Afterwards, a cation aqueous solution and an anion aqueous solution were added into the polar solvent containing the drug-loaded polypeptide-based nanocarrier multiple times for an acid-soluble mineral, for example, calcium phosphate, to be deposited sequentially on the acidic amino acid segment of the drug-loaded polypeptide-based nanocarrier via a mineralization reaction and for formation of a drug-loaded polypeptide-based nanocarrier with an acid-soluble mineralized protective shell, which is an example of the sequentially decomposable polypeptide-based nanocarrier with protective shell of the present invention. According to experiments characterizing the drug-loaded polypeptide-based nanocarrier with protective shell, it has been demonstrated to have high stability in aqueous solutions, high drug loading efficiency, and multi-pH responsiveness. It has also been proved to be able to decompose progressively upon changes in environmental pH, and it shows efficient cellular uptake and high levels of intracellular drug release. Furthermore, it exhibits significant anti-tumor activity and an inhibitory effect on metastatic invasion. Therefore, the sequentially decomposable polypeptide-based nanocarrier with protective shell of the present invention is applicable to manufacture of a pharmaceutical composition by further encapsulating a hydrophobic drug.

Figure 1:
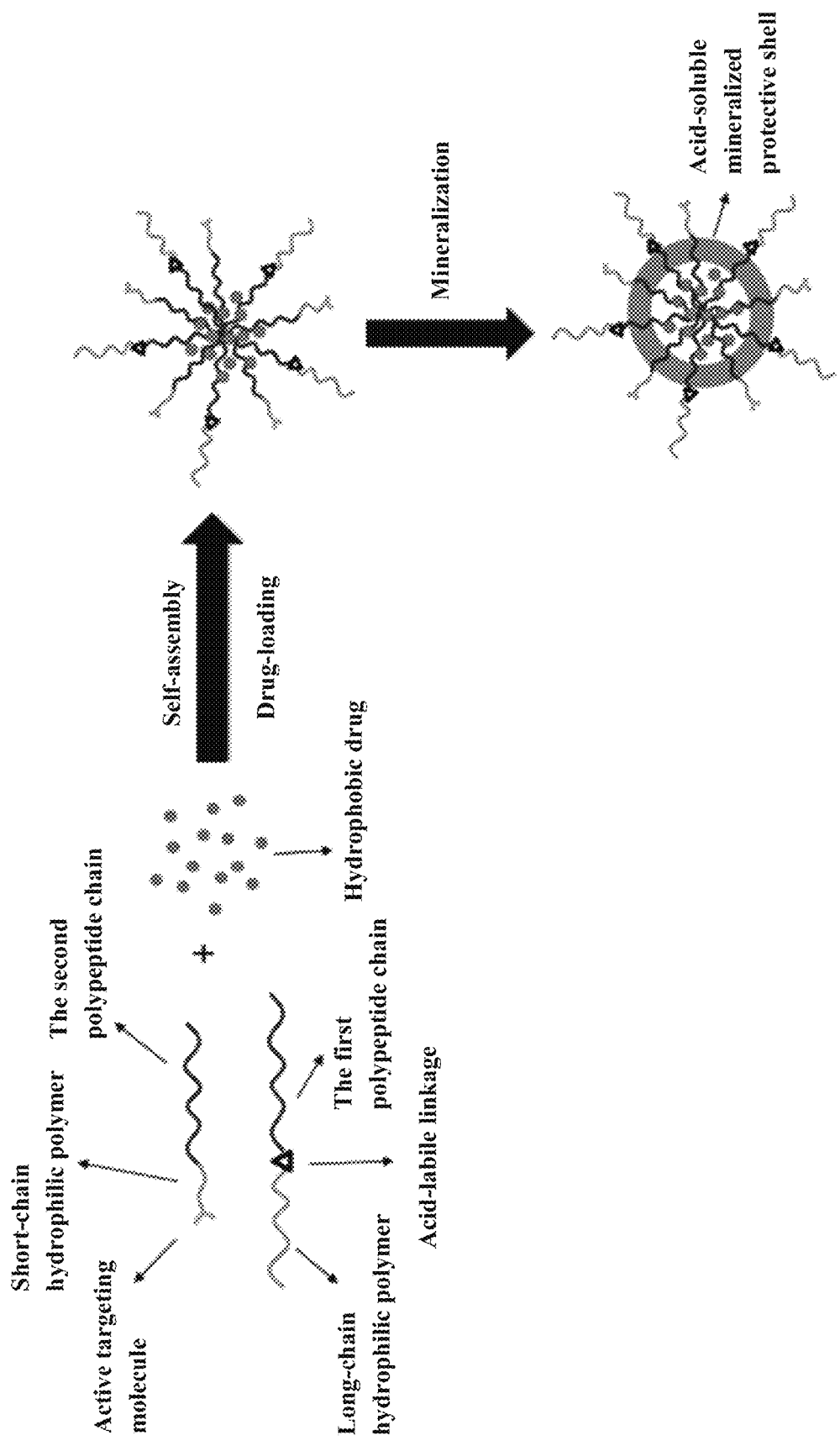
FIG. 1 is a pictorial description of self-assembly of a drug-loaded polypeptide-based nanocarrier with protective shell from the polypeptide-based long chain copolymers and the polypeptide-based short chain copolymers, components of the polypeptide-based nanocarrier with protective shell of the present invention, and a hydrophobic drug.
Figure 2:
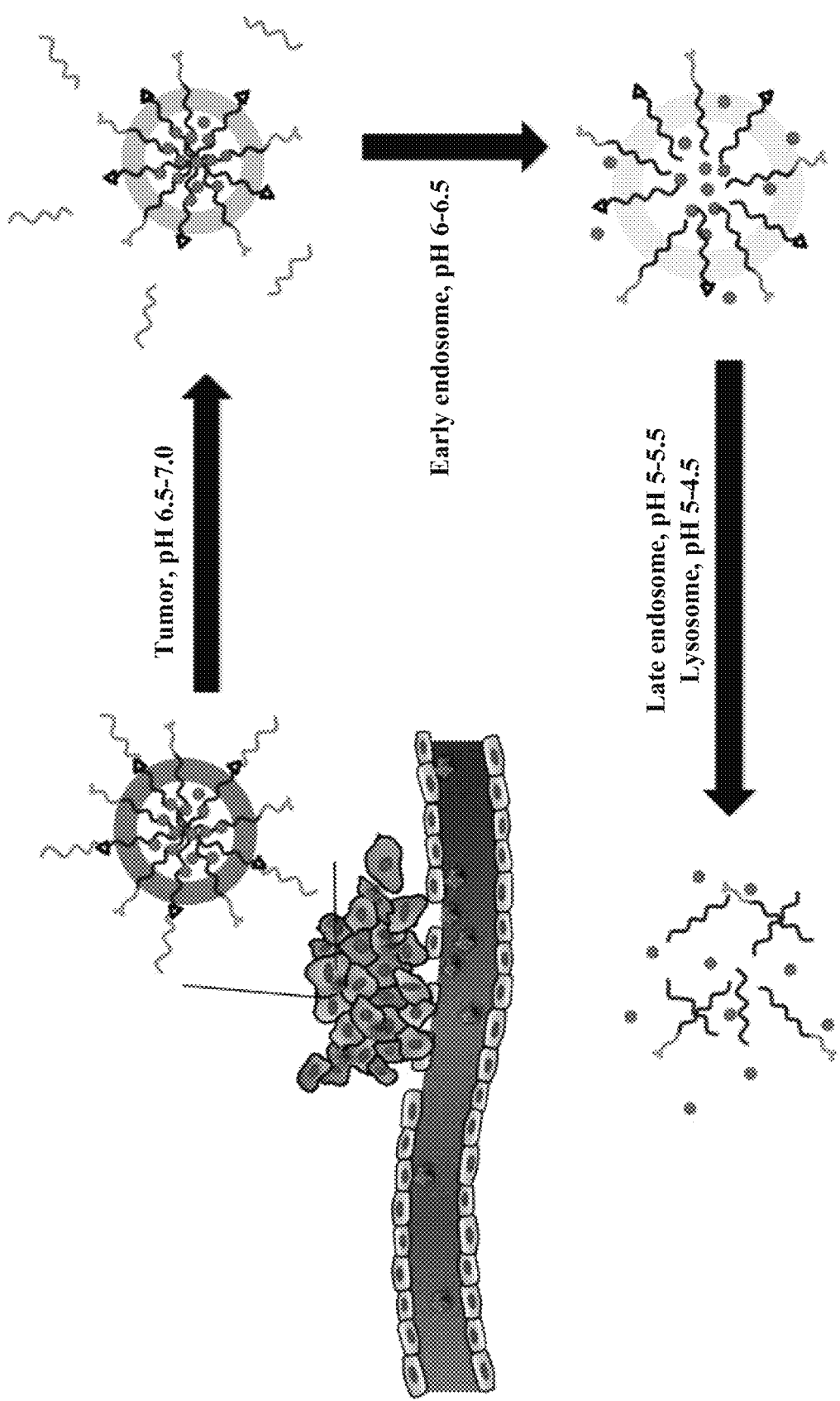
FIG. 2 is a pictorial description of sequential decomposition of the drug-loaded polypeptide-based nanocarrier with protective shell of the present invention upon changes in environmental pH.

As shown in the pictorial description of FIG. 1, the sequentially decomposable polypeptide-based nanocarrier with protective shell of the present invention forms by self-assembly and encapsulates hydrophobic drugs, such as anti-cancer drugs and imaging agents, in the polypeptide core. At the physiological condition of pH 7.4, the acid-responsive amino acid segment of the drug-loaded polypeptide-based nanocarrier with protective shell of the present invention carries no charge and thus offers hydrophobicity required for drug encapsulation along with the hydrophobic amino acid segment. As shown in FIG. 2, it is speculated that when the drug-loaded polypeptide-based nanocarrier with protective shell of the present invention at a size of about 100-200 nm is administered to a subject, it would stably circulate in the blood stream and then penetrate across slits of vascular walls in tumor (at a size of about a hundred to several hundred nanometers) and specifically accumulate in the tumor tissue due to the enhanced permeability and retention (EPR) effect. The slightly acidic environment of the tumor tissue with a pH value of 6.5-7.0 would cause breakage of the acid-labile linkage joining the long-chain hydrophilic polymer to the first polypeptide chain in the drug-loaded polypeptide-based nanocarrier with protective shell, which leads to detachment of the long-chain hydrophilic polymer from the remaining part of the polypeptide-based long chain copolymer and great exposure of the active targeting molecule conjugated with the end of the short-chain hydrophilic polymer in the polypeptide-based short chain copolymer. At the same time, the acid-soluble mineralized protective shell on the acidic amino acid segments of both the polypeptide-based long chain copolymers and the polypeptide-based short chain copolymers would start to slightly dissolve. Once the exposed active targeting molecules binds to receptors on the surface of a target cell in tumor tissue and the drug-loaded polypeptide-based nanocarrier with protective shell gets into the endosome of the target cell through receptor-mediated endocytosis, the more acidic environment with a pH value of 6.0-6.5 in the early endosome would facilitate further dissolution of the acid-soluble mineralized protective shell. Also, this environment causes protonation of the acid-responsive amino acid segments of both the polypeptide-based long chain copolymers and the polypeptide-based short chain copolymers, and the resulting positive charge repulsion brings about size enlargement and structural swelling of the drug-loaded polypeptide-based nanocarrier with protective shell. When the drug-loaded polypeptide-based nanocarrier with protective shell having the swollen structure continues to enter the late endosome and encounter an environmental pH of 5.0-5.5 or a still lower pH of 4.5-5.0 due to fusion of the late endosome and lysosome, the acid-soluble mineralized protective shell would completely dissolve, and therefore the drug-loaded polypeptide-based nanocarrier with protective shell totally decomposes into pieces to allow complete release of drug.

Definition

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the terms "hydrophobic drug" and "hydrophobic agent" are interchangeable. The term "hydrophobic agent" includes hydrophobic drugs for treatment of diseases such as cancers. These drugs include anti-cancer drugs used in chemotherapy, for example, doxorubicin, paclitaxel, and cisplatin, anti-metastatic drugs or agents, for example, matrix metalloproteinase (MMP) inhibitors, angiogenesis inhibitors, and latrunculin B, and substances for gene therapy, for example, plasmid DNA, micro RNA (miRNA), and small interfering RNA (siRNA). The term "hydrophobic agent" also includes hydrophobic imaging agents for diagnosis of diseases such as cancers. These agents include organic materials, inorganic materials, and organic-inorganic hybrid materials, for example, iron oxide, fluorophore, quantum dot, and carbon dot.

Materials and Methods

Materials

Amine-(polyethylene glycol)-carboxylic acid (M.W. 1100 Da; hereinafter referred to as $PEG_{1100}$), doxorubicin hydrochloride (a water soluble salt of doxorubicin, hereinafter referred to as DOX.HCl), 11-ethyl-3-(3-dimethylaminopropyl) m-carbodiimide (EDC), and N-Hydroxysuccinimide (NHS) were purchased from Sigma-Aldrich (St. Louis, Mo., USA). Methoxy polyethylene glycol-amine (M.W. 3400 Da; hereinafter referred to as $PEG_{3400}$) was purchased from NOF (Tokyo, Japan). Cis-aconitic anhydride and dissucinyl suberate (DSS) were purchased from Alfa Aesar (Ward Hill, Mass., USA). 2,4,6-trinitrobenzene sulfonic acid (TNBS) at 5% w/v was purchased from Pierce Chemical (Dallas, Tex., USA). The fluorescent dye DAPI (4',6-diamidino-2-phenylindole) was purchased from Lonza (Basel, Switzerland). The kit of CellTiter 96 Aqueous One Solution Cell Proliferation Assay 1000 assays for cell viability assay (MTS assay) was purchased from Progma (Fitchburg, Wis., USA). GM6001, an inhibitor of matrix metalloproteinases (MMPs), and Latrunculin B were purchased from Abcam (Cambridge, UK). Matrigel® Growth Factor Reduced (GFR) Basement Membrane Matrix was purchased from Corning Inc. (Corning, N.Y., USA). Human recombinant stromal cell-derived factor 1α (SDF-1α, also termed CXCL12) was purchased from Cell Biolabs (San Diego, Calif., USA). Human recombinant epidermal growth factor (EGF) was purchased from R&D systems (Minneapolis, Minn., USA). The fluorescent dye CellTracker™ Green CMFDA (5-chloromethylfluorescein diacetate) was purchased from Molecular Probes (Eugene, Oreg., USA).

Cell Culture

The present invention utilizes human breast adenocarcinoma cell line, MDA-MB-231 (BCRC 60425), and human umbilical vein endothelial cells, HUVEC (BCRC H-UV001), in cell experiments. The MDA-MB-231 cells were cultured in Leibovitz's L-15 medium (Gibco, Thermo Fisher Scientific, Waltham, Mass., USA) supplemented with 10% fetal bovine serum (FBS; Biological Industries, Cromwell, Conn., USA) in the presence of 1% penicillin and streptomycin at 37° C. in 5% $CO_2$. The HUVEC cells were cultured in M199 medium (Gibco, Thermo Fisher Scientific) supplemented with 10% PBS, 30 μg/ml endothelial cell growth supplement (ECGS; Sigma-Aldrich), and 25 U/ml heparin (Sigma-Aldrich) in the presence of 1% penicillin and streptomycin at 37° C. in 5% $CO_2$.

Statistical Analysis

Data are expressed with mean±standard deviation (S.D.). The statistical significance was determined by student's test analysis of variance. * indicates p<0.05,  indicates p<0.01, * indicates p<0.001, and N.S. indicates no significant difference.

Example 1

Preparation of Amphiphilic Molecules of the Polypeptide-Based Long Chain Copolymer and the Polypeptide-Based Short Chain Copolymer This example illustrates the preparation methods of the polypeptide-based long chain copolymer and the polypeptide-based short chain copolymer, the main components of the sequentially decomposable polypeptide-based nanocarrier with protective shell of the present invention. In one preferred embodiment of the present invention, the first polypeptide chain of the polypeptide-based long chain copolymer and the second polypeptide chain of the polypeptide-based short chain copolymer have a common amino acid sequence of 15 glutamic acid residues, 10 histidine residues, and 10 leucine residues from N-terminus to C-terminus, that is, EEEEEEEEEEEEEEEHHHHHHHHHHLLLLLLLLLL (SEQ ID NO:1). The first and the second polypeptide chains with this sequence were purchased from Genscript (Piscataway, N.J., USA). They are collectively denoted as polypeptide $E_{15}$-$H_{10}$-$L_{10}$ (SEQ ID NO:1) in the following examples. However, the residue numbers of glutamic acid, histidine, and leucine are variable, and the preferred residue numbers are 10-20 for glutamic acid, 5-15 for histidine, and 5-15 for leucine. Besides, the long-chain hydrophilic polymer of the polypeptide-based long chain copolymer and the short-chain hydrophilic polymer of the polypeptide-based short chain copolymer are polyethylene glycol with molecular weights of 3400 Da and 1100 Da, which are denoted as $PEG_{3400}$ and $PEG_{1100}$, respectively. For the polypeptide-based long chain copolymer, an acid-labile cis-aconityl linkage was used to conjugate $PEG_{3400}$ to polypeptide $E_{15}$-$H_{10}$-$L_{10}$ (SEQ ID NO:1). For the polypeptide-based short chain copolymer, a stable and noncleavable DSS crosslinker was used to conjugate $PEG_{1100}$ to polypeptide $E_{15}$-$H_{10}$-$L_{10}$ (SEQ ID NO:1), and the $PEG_{1100}$ was conjugated with LyP-1 peptide, an active targeting molecule.

In the following examples, the polypeptide-based long chain copolymer is $PEG_{3400}$-aconityl linkage-polypeptide $E_{15}$-$H_{10}$-$L_{10}$ (SEQ ID NO:1). It was synthesized step by step. At the beginning, $PEG_{3400}$ and cis-aconitic anhydride were dissolved in deionized water and 1,4-dioxane, respectively. The two solutions were mixed and stirred overnight, and a mixture of chloroform and 5% sodium bicarbonate were added into the homogenized solution. After the chloroform layer was removed, the remaining solution was extracted with ethyl acetate. About 5 ml of the extract was transferred into a dialysis membrane (MWCO 1000 Da) for dialysis against 1500 ml deionized water for 4.5 hours, and the dialysate was lyophilized to obtain powder of $PEG_{3400}$-aconitic acid. Next, $PEG_{3400}$-aconitic acid, polypeptide $E_{15}$-$H_{10}$-$L_{10}$ (SEQ ID NO:1), and carboxylate group-activating agents, EDC and NHS, were dissolved in deionized water in a molar ratio of 1:1:10:4. The solution was stirred overnight and transferred into a cellulose membrane tube (MWCO 3000 Da) for filtration. The unfiltered fraction was collected and lyophilized to obtain powder of $PEG_{3400}$-aconityl linkage-polypeptide $E_{15}$-$H_{10}$-$L_{10}$ (SEQ ID NO:1).

In the following examples, the polypeptide-based long chain copolymer is LyP-1 peptide-$PEG_{1100}$-DSS-polypeptide $E_{15}$-$H_{10}$-$L_{10}$ (SEQ ID NO:1). It was synthesized step by step. At the beginning, $PEG_{1100}$ and a ten-fold excess of DSS were dissolved in 2 ml dimethyl sulfoxide (DMSO), and the solution was stirred overnight at pH 7-9. The solution was then dropped into 20 ml cold diethyl ether with a volume ratio of 1:10 (DMSO to diethyl ether) to precipitate $PEG_{1100}$-DSS. The precipitate was collected by centrifugation for 15 minutes, and the supernatant was discarded. The precipitation process was repeated 3 times to remove unreacted DSS, and the final product was collected by centrifugal concentrator (miVac Duo, Japan). Next, $PEG_{1100}$-DSS and polypeptide $E_{15}$-$H_{10}$-$L_{10}$ (SEQ ID NO:1) were dissolved in DMSO, and the solution was stirred overnight at pH 7-9. The solution was then transferred into a dialysis membrane (MWCO 1000 Da) for dialysis against 1500 ml deionized water for 4.5 hours, and the dialysate was lyophilized to obtain powder of $PEG_{1100}$-DSS-polypeptide $E_{15}$-$H_{10}$-$L_{10}$ (SEQ ID NO:1), which was stored at −20° C.

To enable the sequentially decomposable polypeptide-based nanocarrier with protective shell of the present invention to target tumor tissue, the end of $PEG_{1100}$ of $PEG_{1100}$-DSS-polypeptide $E_{15}$-$H_{10}$-$L_{10}$ (SEQ ID NO:1) was conjugated with LyP-1 peptide, an active targeting molecule to tumor cells, endothelial cells, and lymphatic cells in breast cancer tissue, by chemical grafting. The LyP-1 cyclic peptide with a sequence of CGNKRTRGC (SEQ ID NO:2) was purchased from Genscript (Piscataway, N.J., USA). For preparation, $PEG_{1100}$-DSS-polypeptide $E_{15}$-$H_{10}$-$L_{10}$ (SEQ ID NO:1), LyP-1 cyclic peptide, and carboxylate group-activating agents, EDC and NHS, were dissolved in the mixture of deionized water and DMSO in a molar ratio of 1:1:10:4. The solution was stirred overnight and transferred into a cellulose membrane tube (MWCO 3000 Da) for filtration. The unfiltered fraction was collected and lyophilized to obtain powder of LyP-1 peptide-$PEG_{1100}$-DSS-polypeptide $E_{15}$-$H_{10}$-$L_{10}$ (SEQ ID NO:1), which was stored at −20° C.

To verify that the polypeptide-based long chain copolymer and the polypeptide-based short chain copolymer were successfully synthesized, nuclear magnetic resonance (NMR) spectral analysis and Fourier transform infrared (FTIR) spectral analysis were performed to determine the chemical structures. NMR spectra were recorded on a Varian Unity Inova 500 NMR spectrometer operating at 500 MHz. The test samples were prepared as follows: the synthetic product of each step for preparing the polypeptide-based long chain copolymer was dissolved in $D_2O$ at a concentration of 1 mg/ml; among the synthetic product of each step for preparing the polypeptide-based short chain copolymer, $PEG_{1100}$ and $PEG_{1100}$-DSS were dissolved in $CDCl_3$, and $PEG_{1100}$-DSS-polypeptide $E_{15}$-$H_{10}$-$L_{10}$ (SEQ ID NO:1) and LyP-1 peptide-$PEG_{1100}$-DSS-polypeptide $E_{15}$-$H_{10}$-$L_{10}$ (SEQ ID NO:1) were dissolved in DMSO-d6, each of which was at a concentration of 1 mg/ml. FTIR spectra were recorded on a Vertex 80v FTIR spectrometer (Bruker, Billerica, Mass., USA). The test samples were tablets of the polypeptide-based long chain copolymer, the polypeptide-based short chain copolymer without LyP-1 peptide, and constituents thereof prepared by compression of corresponding powders.

Figure 3A:
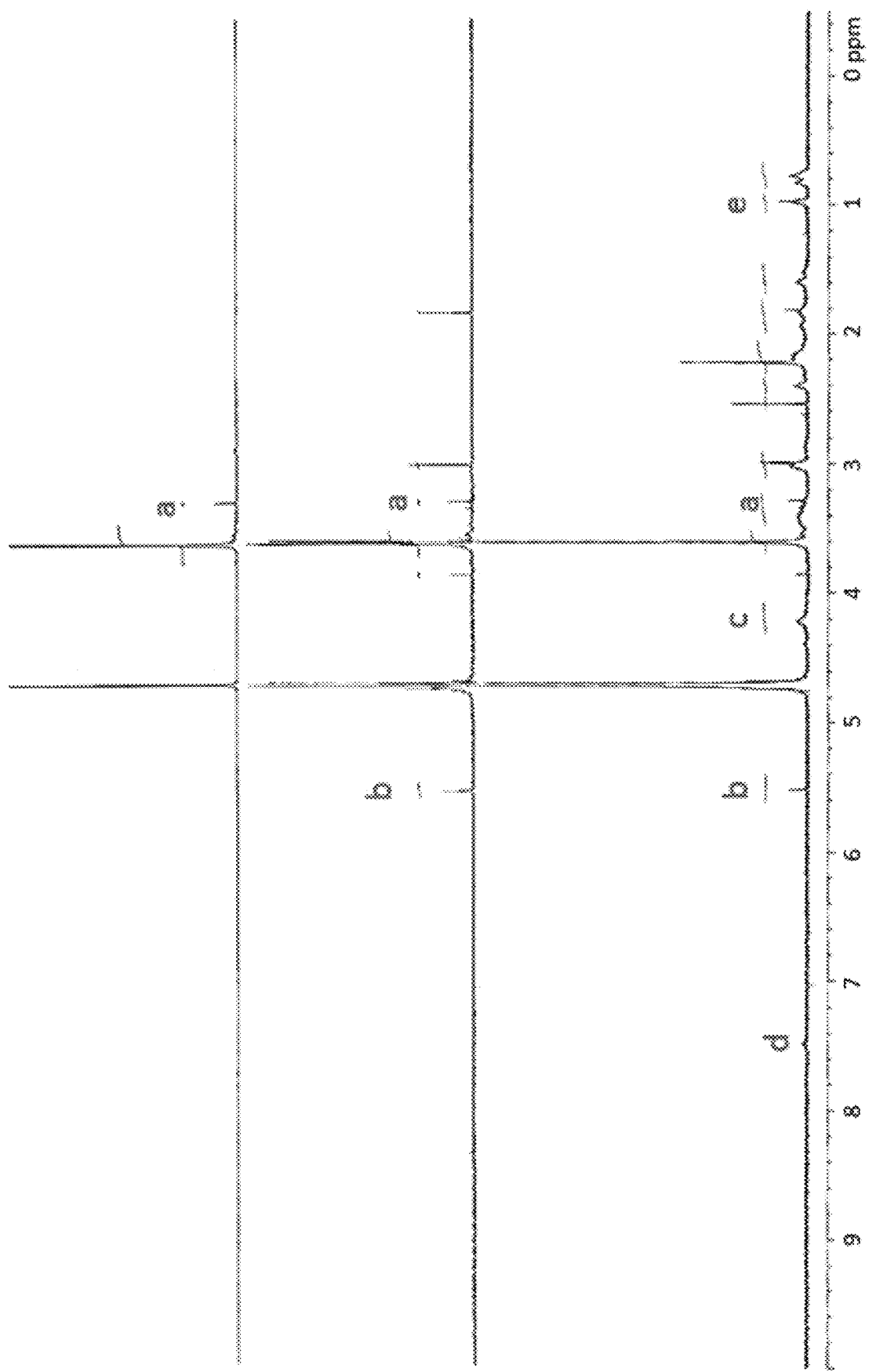
FIG. 3A shows comparison between the $^1$H NMR spectra of the polypeptide-based long chain copolymer and the synthetic product of each step for preparing the same; the spectra of $PEG_{3400}$, $PEG_{3400}$-aconitic acid, and $PEG_{3400}$-aconityl linkage-polypeptide $E_{15}$-$H_{10}$-$L_{10}$ are sequentially shown from top panel to bottom panel.

The $^1H$ NMR spectra of the polypeptide-based long chain copolymer and the synthetic product of each step for preparing the same are compared in FIG. 3A, which sequentially shows the spectra of $PEG_{3400}$, $PEG_{3400}$-aconitic acid, and $PEG_{3400}$-aconityl linkage-polypeptide $E_{15}$-$H_{10}$-$L_{10}$ (SEQ ID NO:1) from top panel to bottom panel. The characteristic peak of polyethylene glycol, peak a in FIG. 3A, was observed in the spectra of $PEG_{3400}$, $PEG_{3400}$-aconitic acid, and $PEG_{3400}$-aconityl linkage-polypeptide $E_{15}$-$H_{10}$-$L_{10}$ (SEQ ID NO:1). The peak of amide formation between polyethylene glycol and aconitic anhydride, peak b in FIG. 3A, was observed in the spectra of $PEG_{3400}$-aconitic acid, and $PEG_{3400}$-aconityl linkage-polypeptide $E_{15}$-$H_{10}$-$L_{10}$ (SEQ ID NO:1). The peaks of polypeptide, peaks c-e in FIG. 3A, were observed in the spectrum of $PEG_{3400}$-aconityl linkage-polypeptide $E_{15}$-$H_{10}$-$L_{10}$ (SEQ ID NO:1). The characteristic peak at 4.8 ppm in FIG. 3A was resulted from $D_2O$.

Figure 3B:
FIG. 3B shows comparison between the $^1$H NMR spectra of the polypeptide-based short chain copolymer and the synthetic product of each step for preparing the same; the spectra of $PEG_{1100}$, $PEG_{1100}$-DSS, $PEG_{1100}$-DSS-polypeptide $E_{15}$-$H_{10}$-$L_{10}$, and LyP-1 peptide-$PEG_{1100}$-DSS-polypeptide $E_{15}$-$H_{10}$-$L_{10}$ are sequentially shown from top panel to bottom panel.

The $^1H$ NMR spectra of the polypeptide-based short chain copolymer and the synthetic product of each step for preparing the same are compared in FIG. 3B, which sequentially shows the spectra of $PEG_{1100}$, $PEG_{1100}$-DSS, $PEG_{1100}$-DSS-polypeptide $E_{15}$-$H_{10}$-$L_{10}$ (SEQ ID NO:1), and LyP-1 peptide-$PEG_{1100}$-DSS-polypeptide $E_{15}$-$H_{10}$-$L_{10}$ (SEQ ID NO:1) from top panel to bottom panel. The characteristic peak of polyethylene glycol, peaks a-b in FIG. 3B, was observed in the spectra of $PEG_{1100}$, $PEG_{1100}$-DSS, $PEG_{1100}$-DSS-polypeptide $E_{15}$-$H_{10}$-$L_{10}$ (SEQ ID NO:1), and LyP-1 peptide-$PEG_{1100}$-DSS-polypeptide $E_{15}$-$H_{10}$-$L_{10}$ (SEQ ID NO:1). The peak of NHS ester in $PEG_{1100}$-DSS, peak c in FIG. 3B, was observed in the spectrum of $PEG_{1100}$-DSS, but this peak disappeared in the spectra of $PEG_{1100}$-DSS-polypeptide $E_{15}$-$H_{10}$-$L_{10}$ (SEQ ID NO:1) due to conjugation of $PEG_{1100}$-DSS to polypeptide $E_{15}$-$H_{10}$-$L_{10}$ (SEQ ID NO:1). The peaks of polypeptide were observed in the spectra of $PEG_{1100}$-DSS-polypeptide $E_{15}$-$H_{10}$-$L_{10}$ (SEQ ID NO:1) and LyP-1 peptide-$PEG_{1100}$-DSS-polypeptide $E_{15}$-$H_{10}$-$L_{10}$ (SEQ ID NO:1). The peaks of amino acids in LyP-1, such as peaks from 2.6 ppm to 2.8 ppm for asparagine and lysine, were observed in the spectrum of LyP-1 peptide-$PEG_{1100}$-DSS-polypeptide $E_{15}$-$H_{10}$-$L_{10}$ (SEQ ID NO:1). The characteristic peaks at 7.24 ppm and 2.5 ppm in FIG. 3B were resulted from $CDCl_3$ and DMSO-d6, respectively.

Figure 4A:
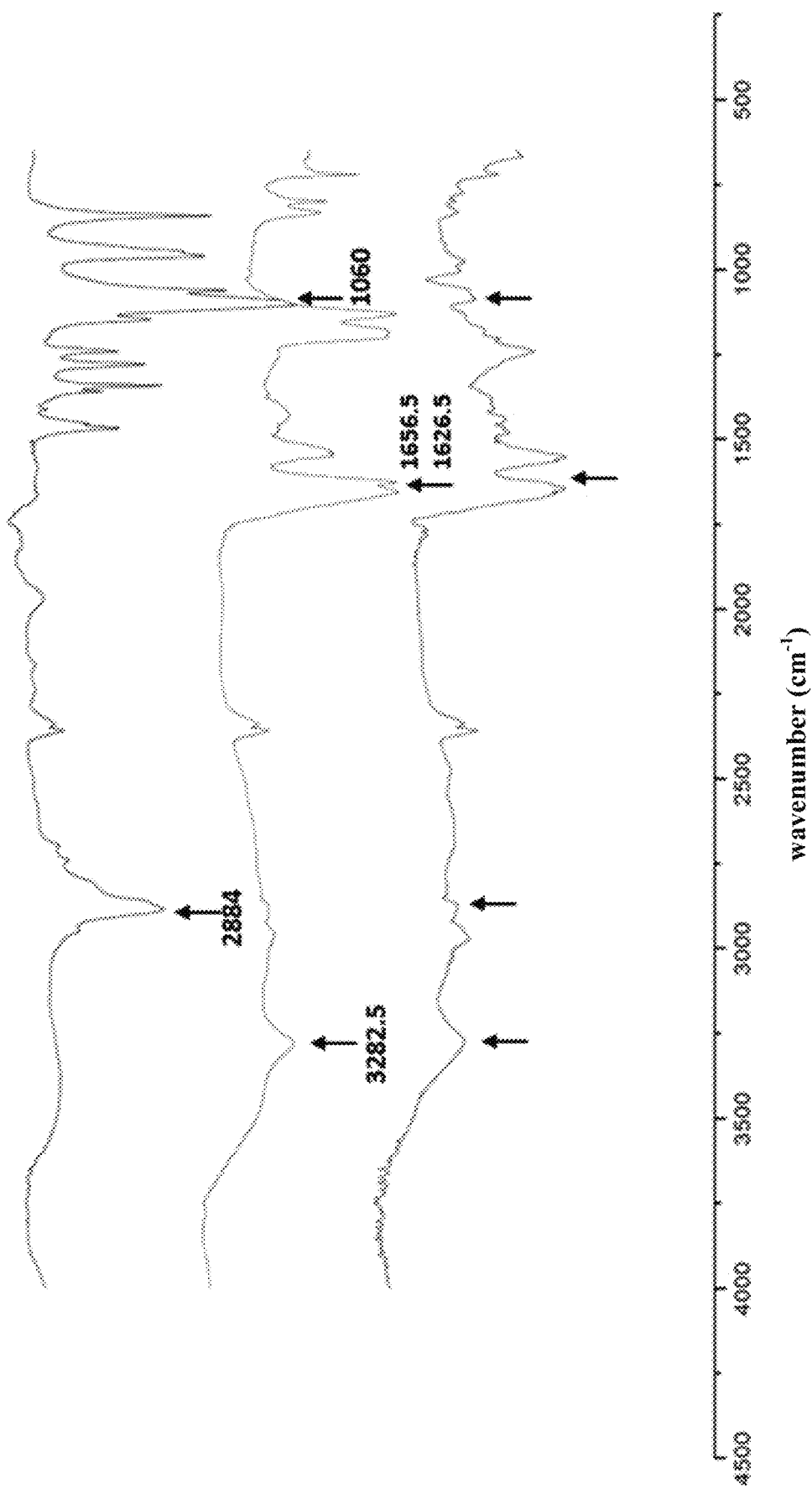
FIG. 4A shows comparison between the FTIR spectra of the polypeptide-based long chain copolymer and constituents thereof; the spectra of $PEG_{3400}$, polypeptide $E_{15}$-$H_{10}$-$L_{10}$, and $PEG_{3400}$-aconityl linkage-polypeptide $E_{15}$-$H_{10}$-$L_{10}$ are sequentially shown from top panel to bottom panel.

The FTIR spectra of the polypeptide-based long chain copolymer and constituents thereof are compared in FIG. 4A, which sequentially shows the spectra of $PEG_{3400}$, polypeptide $E_{15}$-$H_{10}$-$L_{10}$ (SEQ ID NO:1), and $PEG_{3400}$-aconityl linkage-polypeptide $E_{15}$-$H_{10}$-$L_{10}$ (SEQ ID NO:1) from top panel to bottom panel with arrows indicating characteristic absorption peaks. The peak of alkane absorption at 2884 $cm^{-1}$ and the peak of alkyl ether absorption at 1060 $cm^{-1}$ for polyethylene glycol were observed in the spectra of $PEG_{3400}$ and $PEG_{3400}$-aconityl linkage-polypeptide $E_{15}$-$H_{10}$-$L_{10}$ (SEQ ID NO:1). The peak of amide absorption at 3282.5 $cm^{-1}$ and the peaks of ester absorption at 1626.5 $cm^{-1}$ and 1656.5 $cm^{-1}$ for polypeptide was observed in the spectra of polypeptide $E_{15}$-$H_{10}$-$L_{10}$ (SEQ ID NO:1) and $PEG_{3400}$-aconityl linkage-polypeptide $E_{15}$-$H_{10}$-$L_{10}$ (SEQ ID NO:1).

Figure 4B:
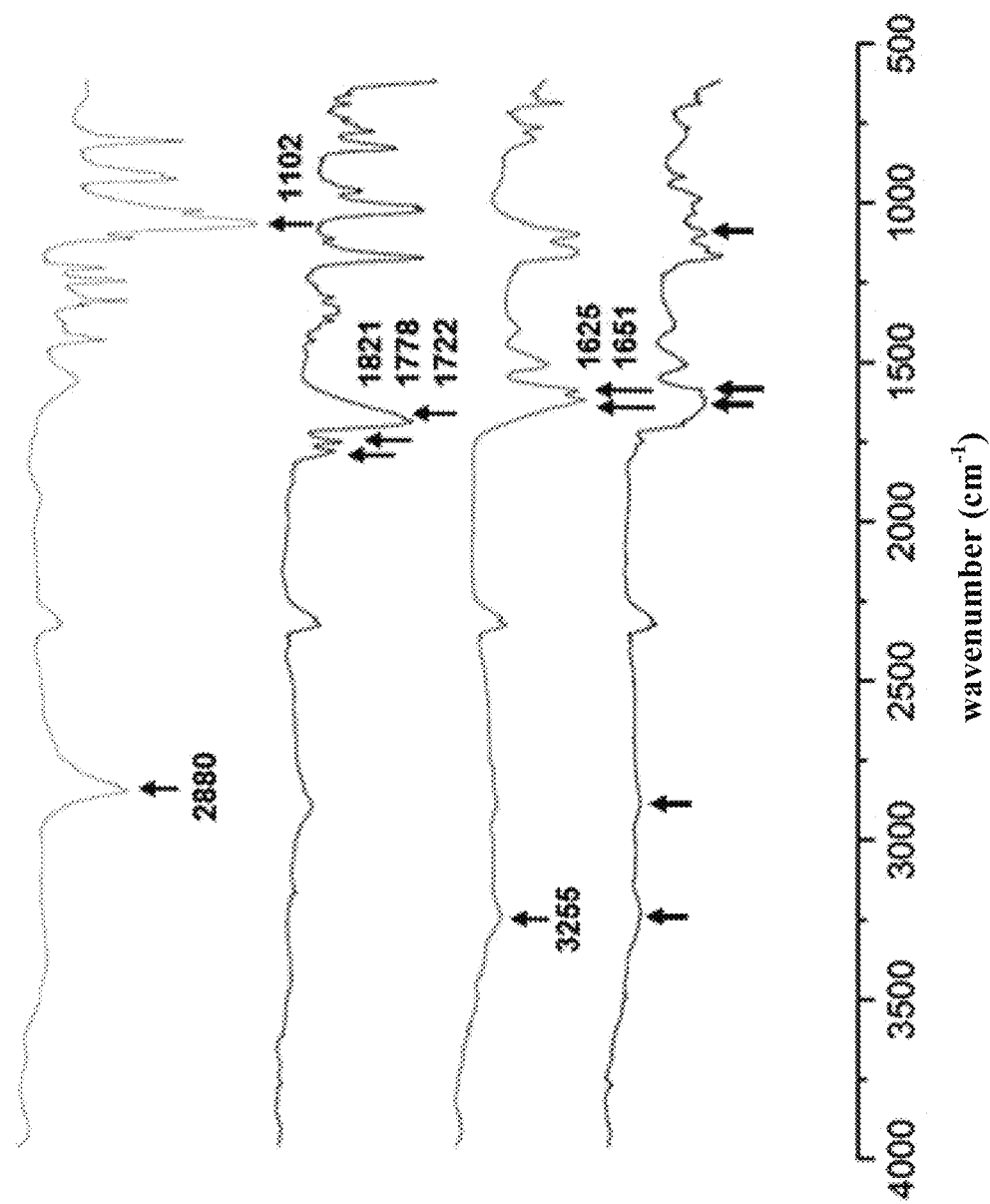
FIG. 4B shows comparison between the FTIR spectra of the polypeptide-based short chain copolymer without LyP-1 peptide and constituents thereof; the spectra of $PEG_{1100}$, DSS, polypeptide $E_{15}$-$H_{10}$-$L_{10}$, and $PEG_{1100}$-DSS-polypeptide $E_{15}$-$H_{10}$-$L_{10}$ are sequentially shown from top panel to bottom panel.

The FTIR spectra of the polypeptide-based short chain copolymer without LyP-1 peptide and constituents thereof are compared in FIG. 4B, which sequentially shows the spectra of $PEG_{1100}$, DSS, polypeptide $E_{15}$-$H_{10}$-$L_{10}$ (SEQ ID NO:1), and $PEG_{1100}$-DSS-polypeptide $E_{15}$-$H_{10}$-$L_{10}$ (SEQ ID NO:1) from top panel to bottom panel with arrows indicating characteristic absorption peaks. The peak of alkane absorption at 2880 $cm^{-1}$ and the peak of alkyl ether absorption at 1102 $cm^{-1}$ from $PEG_{1100}$ were observed in the spectrum of $PEG_{1100}$. The peak of amide absorption at 3255 $cm^{-1}$ and the peaks of ester absorption at 1625 $cm^{-1}$ and 1651 $cm^{-1}$ from polypeptide were observed in the spectra of polypeptide $E_{15}$-$H_{10}$-$L_{10}$ (SEQ ID NO:1) and $PEG_{1100}$-DSS-polypeptide $E_{15}$-$H_{10}$-$L_{10}$ (SEQ ID NO:1). In addition, the peaks at 1722 $cm^{-1}$, 1778 $cm^{-1}$, and 1821 $cm^{-1}$ for DSS disappeared in the spectrum of $PEG_{1100}$-DSS-polypeptide $E_{15}$-$H_{10}$-$L_{10}$ (SEQ ID NO:1).

The results mentioned above indicate that the polypeptide-based long chain copolymer and the polypeptide-based short chain copolymer may be successfully prepared by chemical grafting illustrated in this example.

Example 2

Preparation of the Drug-Loaded Polypeptide-Based Nanocarrier with Protective Shell This example illustrates preparation of a drug-loaded polypeptide-based nanocarrier from the previously described polypeptide-base long chain copolymer, the polypeptide-based short chain copolymer, and a hydrophobic drug, such as the anti-cancer drug doxorubicin (DOX), and formation of the drug-loaded polypeptide-based nanocarrier with protective shell by deposition of calcium phosphate on the negatively charged acidic amino acid segment of the drug-loaded polypeptide-based nanocarrier via a mineralization reaction. At the beginning, the doxorubicin hydrochloride (DOX.HCl) was mixed with triethylamine in a molar ratio of 1:3 in DMSO and the resulting concentration of DOX.HCl was 3.4 mM. The solution was stirred overnight and was added into a DMSO solution containing the polypeptide-base long chain copolymer and the polypeptide-based short chain copolymer in a molar ratio of about 1:1 (the concentrations of both the polypeptide-based long chain copolymer and the polypeptide-based short chain copolymer were about 1.34 mM). In one preferred embodiment of the present invention, the molar ratio of the polypeptide-based long chain copolymer and the polypeptide-based short chain copolymer may be adjusted but not limited to about 1:2 or 2:1. The mixed solution was stirred in the dark at room temperature, and the polypeptide-base long chain copolymer and the polypeptide-based short chain copolymer would encapsulate DOX and self-assemble into the drug-loaded polypeptide-based nanocarriers dispersed in the mixed solution. The mixed solution was transferred into a cellulose membrane tube (MWCO 1000 Da) to remove the free drug, DOX in this example, and was subjected to lyophilization to obtain powder of the drug (DOX)-loaded polypeptide-based nanocarriers, which was stored at −20° C.

To increase stability of the abovementioned drug-loaded polypeptide-based nanocarrier and decrease drug leakage before reaching the target tissue, the present invention exploits the negatively charged acidic amino acid segment of the polypeptide of the drug-loaded polypeptide-based nanocarrier for sequential deposition of an acid-soluble mineral thereon, for example, calcium phosphate and calcium carbonate. In one preferred embodiment of the present invention, a mineralized protective shell of calcium phosphate is formed on the glutamic acid segment of the polypeptide $E_{15}$-$H_{10}$-$L_{10}$ (SEQ ID NO:1). The preparation method is illustrated as follows. A 0.02 M calcium chloride aqueous solution and then a 0.02 M sodium hydrogen phosphate aqueous solution were separately added into the previously described mixed solution containing the dispersed drug-loaded polypeptide-based nanocarriers with continuous stirring. This step of adding the calcium ion aqueous solution and the phosphate aqueous solution was repeated at least 5 times, preferably at least 10 times. When the addition step was repeated 10 times or more, the initial additions were accompanied by low-speed stirring, and the following additions were accompanied by high-speed stirring. To remove the unreacted ionic species, the mixed solution was transferred into a dialysis membrane (MWCO 1000 Da) for dialysis against excess deionized water. The dialysate was lyophilized to obtain powder of the drug-loaded polypeptide-based nanocarrier with protective shell, which was stored at −20° C. When an acid-soluble mineralized protective shell of calcium carbonate is requested, the anion aqueous solution in the abovementioned step would be a carbonate aqueous solution.

The sequentially decomposable polypeptide-based nanocarrier with protective shell of the present invention may be equipped with protective shells in response to other stimuli when the amino acid sequence of the first polypeptide chain and the second polypeptide chain of the nanocarrier is changed. For example, when the first polypeptide chain of the polypeptide-based long chain copolymer and the second polypeptide chain of the polypeptide-based short chain copolymer have cysteine segments, which are able to form disulfide bonds, in place of the acidic amino acid segments, the self-assembled polypeptide-based nanocarrier with protective shell would carry a redox-responsive protective shell. This is due to formation of disulfide bonds upon oxidation between the cysteine segments of the polypeptide-based long chain copolymer and the polypeptide-based short chain copolymer in proximity to each other and the resulting crosslinking between the polypeptide-based long chain copolymer and the polypeptide-based short chain copolymer in the polypeptide-based nanocarrier with protective shell. In the oxidizing environment outside of cells, this polypeptide-based nanocarrier with protective shell stably encapsulates drugs because of its intact redox-responsive protective shell. Yet, when it is taken up by cells, the redox-responsive protective shell of the polypeptide-based nanocarrier with protective shell would decompose gradually because the disulfide bonds are broken upon reduction by intracellular glutathione S-transferase (GST), and thus release of drug would be promoted.

Example 3

Hydrolysis Profile of the Acid-Labile Aconityl Linkage in the Polypeptide-Based Long Chain Copolymer TNBS (2,4,6-trinitrobenzene sulfonic acid) assay was performed in this example to analyze the acidic hydrolysis of the cis-aconityl linkage in the polypeptide-based long chain copolymer in conditions of different pH values. TNBS reacts with primary amines to yield a soluble orange colored product. Since $PEG_{3400}$ released from hydrolyzed $PEG_{3400}$-aconitic acid carries a free amine group at the end, the hydrolysis level of $PEG_{3400}$-aconitic acid at different pH values is determined based on the amount of the colored product formed in TNBS assay. $PEG_{3400}$-aconitic acid (2 mg/ml) was first dissolved in deionized water with a pH value of 5.0, 6.5, or 7.4 for hydrolysis. The hydrolysis reactions of 3 hours, 6 hours, 12 hours, and 24 fours were stopped by adjusting the pH value of the $PEG_{3400}$-aconitic acid hydrolysate solutions to 8.2 and freezing. Sodium bicarbonate was added to the abovementioned hydrolysate solutions to a final concentration of 0.1 M (pH 8.2), and a 5% w/v TNBS solution was then added for reaction at 37° C. for 1 hour. The reaction was terminated using 1.0 N HCl, so that the volume ratio of the $PEG_{3400}$-aconitic acid hydrolysate solution, the TNBS solution, and HCl was 4:2:1. Absorbance of the reaction-terminated solutions at 335 nm was measured with an enzyme-linked immunosorbent assay (ELISA) reader (Victor X3 2030 Multilabel Reader, PerkinElmer, Waltham, Mass., USA). According to the standard curve obtained from amine samples with known concentration, free amine group of $PEG_{3400}$ in the reaction-terminated solutions was quantified and the hydrolysis level of $PEG_{3400}$-aconitic acid at each pH was calculated.

Figure 5:
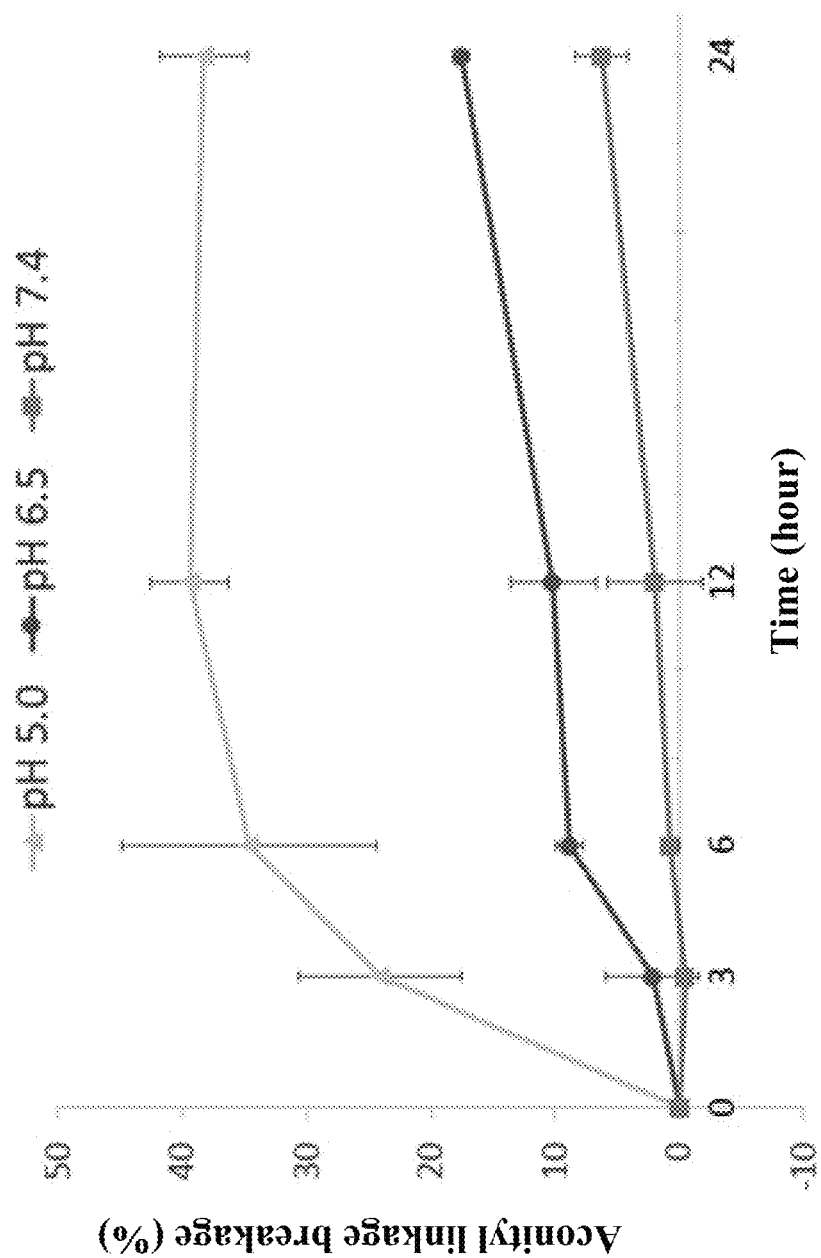
FIG. 5 shows hydrolysis profiles of the cis-aconityl linkage in the polypeptide-based long chain copolymer at different pH values.

As shown in FIG. 5, within 12 hours, breakage of the cis-aconityl linkage at pH 7.4 was about 1.97%, while that at pH 6.5 and pH 5 were 13.28% and 43.33%. At pH 5, the hydrolysis reached plateau after 12 hours. On the other hand, the hydrolysis at pH 6.5 continued within 24 hours and achieved 21% breakage of the cis-aconityl linkage. The results indicate that in response to decreasing pH in the environment, for example, from pH 7.4 down to pH 6.5, there is increasing hydrolysis of the cis-aconityl linkage in the polypeptide-based long chain copolymer of the polypeptide-based nanocarrier with protective shell of the present invention.

Example 4

Characterization of the Drug-Loaded Polypeptide-Based Nanocarrier with Protective Shell To evaluate the difference in particle size and stability between the drug-loaded polypeptide-based nanocarrier with protective shell of the present invention and the drug-loaded polypeptide-based nanocarrier without protective shell at different pH values, dynamic light scattering (DLS) analysis and zeta potential analysis were performed in this example to compare the size distribution and surface charge of the DOX-loaded polypeptide-based nanocarrier with protective shell of calcium phosphate of the present invention and the DOX-loaded polypeptide-based nanocarrier without protective shell. In addition, transmission electron microscopy (TEM) was utilized to examine the surface morphology of the drug-loaded polypeptide-based nanocarrier with protective shell of the present invention. Also, the drug loading content (weight of the encapsulated drug/weight of the drug-loaded nanocarrier×100%) and the drug loading efficiency (the amount of the encapsulated drug/the amount of drug feeding as the drug-loaded nanocarrier is prepared× 100%) were determined for the two types of polypeptide-based nanocarriers using a visible-ultraviolet spectrophotometer.

The DLS analysis and the zeta potential analysis were carried out on Malvern Zetasizer Nano ZS ZEN3600 (Malvern Instruments Ltd., Worcestershire, UK) to determine the average size, the polydispersity index (PDI), and the zeta potential of the abovementioned two types of polypeptide-based nanocarriers (1 mg/ml) in deionized water at pH 5.0 or pH 7.4. As shown in TABLE 1, at pH 7.4, the drug-loaded polypeptide-based nanocarriers without protective shell (DOX NP) had an average size of about 77.5±3.8 nm, a zeta potential of about −45.5±1.0 mV, a drug loading content of 10.22%, and a drug loading efficiency of 55.17%. Comparatively, the drug-loaded polypeptide-based nanocarriers with protective shell (M-DOX NP) possessed a larger size of 179.4±33.9 nm, a less negative surface charge of −21.9±1.6 mV, a lower loading content of 8.16%, and a similar loading efficiency of 56.33%. In the acidic environment, such as at pH 5, the abovementioned two types of polypeptide-based nanocarriers both approximately doubled their sizes and had a zeta potential from negative to positive. These results indicate that the two types of polypeptide-based nanocarriers are stably dispersed in solutions at pH 7.4, whereas they are less stable in solutions and swollen in structure at pH 5 due to protonation of the acid-responsive segment, in this example, the histidine segment.

TABLE 1

| Sample | Size (nm) | PDI | Zeta potential (mV) |
| --- | --- | --- | --- |
| DOX NP, pH 7.4 | 77.5 ± 3.8 | 0.255 | −45.5 ± 1.0 |
| DOX NP, pH 5.0 | 143.7 ± 6.6 | 0.200 | 22.5 ± 1.0 |
| M-DOX NP, pH 7.4 | 179.4 ± 33.9 | 0.437 | −21.9 ± 1.6 |
| M-DOX NP, pH 5.0 | 291.2 ± 25.1 | 0.427 | 21.7 ± 2.1 |

The TEM images of the drug-loaded polypeptide-based nanocarriers with protective shell were obtained using a Hitachi H-7650 transmission electron microscope (120 kV, Tokyo, Japan). The TEM samples were prepared by dropping 5 μl of a freshly prepared aqueous solution (3 mg/ml) of the drug-loaded polypeptide-based nanocarriers with protective shell onto a copper grid coated with Formvar film. After 30-second deposition, the aqueous droplet was blotted away with filter paper. These steps were repeated 3 times, and then the samples were dried overnight at room temperature.

Figure 6B:
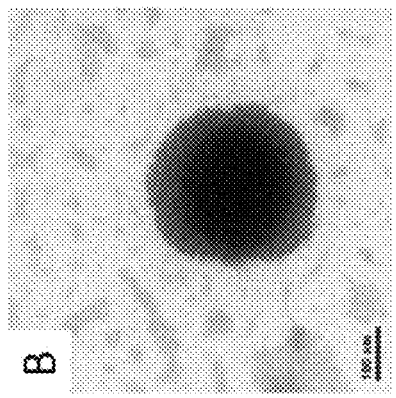
FIGS. 6A-6F show transmission electron microscopy (TEM) images of the DOX-loaded polypeptide-based nanocarriers with protective shell of calcium phosphate of the present invention.
Figure 6A:
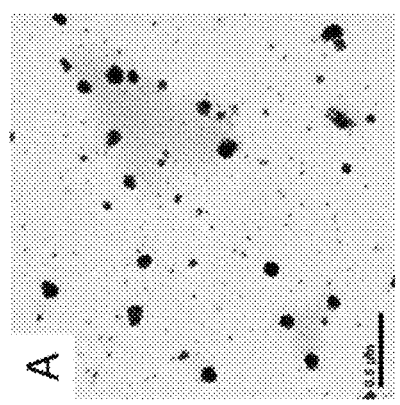
Figure 6D:
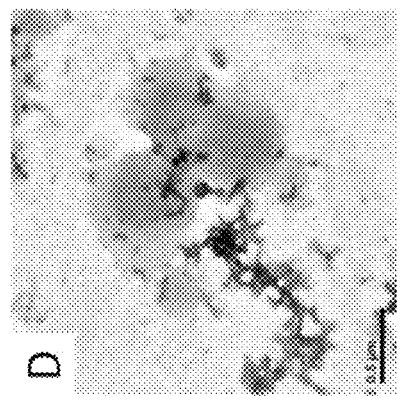
Figure 6C:
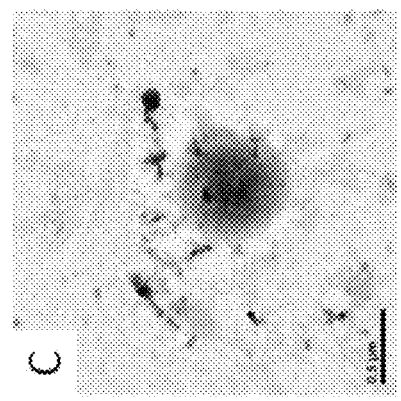
Figure 6F:
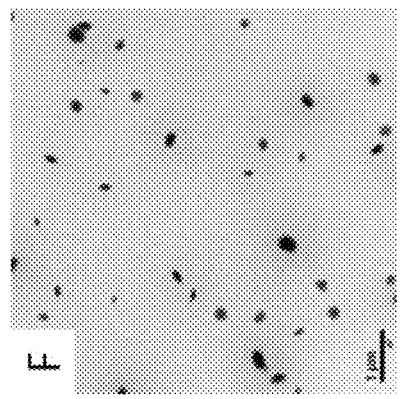
Figure 6E:
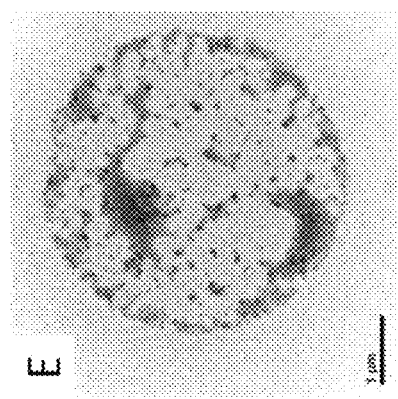

As shown in FIG. 6A, the drug-loaded polypeptide-based nanocarriers with protective shell at pH 7.4 had spherical shape and favorable dispersity, which corresponded to the results from DLS analysis. More specifically, as shown in FIG. 6B, the structures of the polypeptide core and the outer layer of hydrophilic polymer in the drug-loaded polypeptide-based nanocarrier with protective shell were clearly observed. The polypeptide core looked dark gray because the outermost part of the polypeptide core comprised the mineralized protective shell of calcium phosphate, while the outer layer of hydrophilic polymer corresponded to the surrounding area that looked light gray. As shown in FIGS. 6C-6F, after acid treatment such as pH down to 5 for 20 minutes, 40 minutes, 1 hour, and about 4 hours, the drug-loaded polypeptide-based nanocarrier with protective shell progressively collapsed. According to FIGS. 6C-6D, after acidic treatment for a short time, the mineralized protective shell of calcium phosphate (dark gray) in the drug-loaded polypeptide-based nanocarrier with protective shell started to dissolve, while the spherical structure formed from both the polypeptide-based long chain copolymer and the polypeptide-based short chain copolymer (light gray) remained. According to FIG. 6E, within 1 hour, the drug-loaded polypeptide-based nanocarrier with protective shell swelled to a size of over 4 μm, which indicated that protonation of the histidine segment at a low pH and the resulting positive charge repulsion that occurred in the polypeptide core facilitated the drug-loaded polypeptide-based nanocarrier with protective shell to swell and decompose. After 4 hours, the drug-loaded polypeptide-based nanocarrier with protective shell completely collapsed with several recrystallized calcium phosphate in the shape of oval as shown in FIG. 6F. These results indicate that the drug-loaded polypeptide-based nanocarrier with protective shell of the present invention possesses an intact spherical structure at the physiological condition, which contributes to stable encapsulation of drugs. However, the drug-loaded polypeptide-based nanocarrier with protective shell progressively decomposes at pH 5, which facilitates drug release.

Example 5 pH-Responsive Drug Release of the Drug-Loaded Polypeptide-Based Nanocarrier with Protective Shell To verify that the drug-loaded polypeptide-based nanocarrier with protective shell of the present invention releases drugs in response to a decrease of the environmental pH, a visible-ultraviolet spectrophotometer was used in this example to determine the drug release profiles of the DOX-loaded polypeptide-based nanocarrier with protective shell of calcium phosphate of the present invention and the DOX-loaded polypeptide-based nanocarrier without protective shell in solutions at different pH values. Each of the abovementioned two types of polypeptide-based nanocarriers at 1 mg/ml in phosphate buffered saline (PBS; sodium chloride 136.9 mM, potassium chloride 2.68 mM, sodium hydrogen phosphate 8.06 mM, and potassium dihydrogen phosphate 1.47 mM) at pH 5.0 or pH 7.4 was sealed in a dialysis membrane (MWCO 1000 Da) and then immersed in a vial of 20 ml PBS at pH 5.0 or pH 7.4, respectively. The vials were shaken at a speed of 150 rpm at 37° C. The PBS was replaced with fresh PBS at prescribed time points for determination of the content of the released drug therein. The DOX spectrum was obtained with an excitation wavelength at 490 nm and an emission wavelength at 535 nm.

Figure 7:
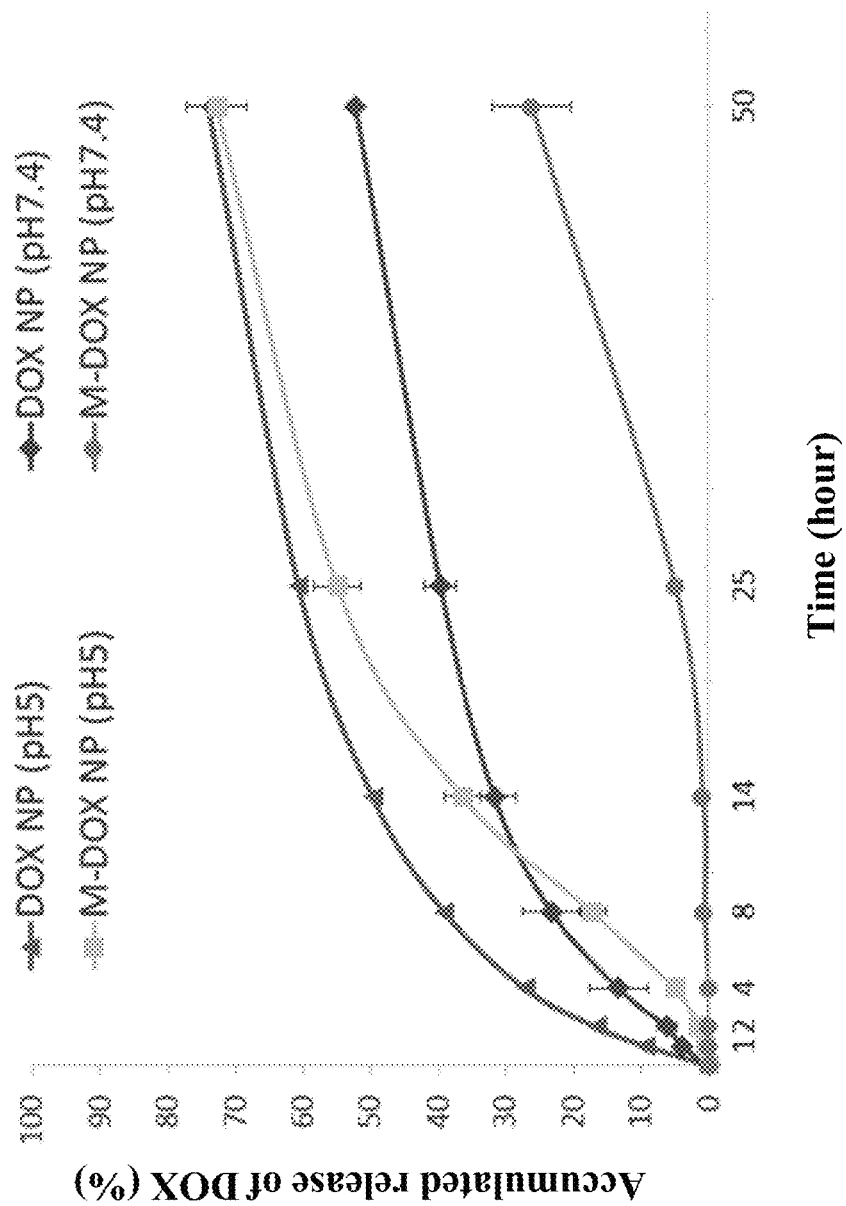
FIG. 7 shows accumulated DOX release profiles of the DOX-loaded polypeptide-based nanocarriers without protective shell (DOX NP) and the DOX-loaded polypeptide-based nanocarriers with protective shell of calcium phosphate (M-DOX NP) of the present invention at different pH values.

As shown in FIG. 7, the drug-loaded polypeptide-based nanocarriers without protective shell (DOX NP) demonstrated initial burst release of drug. In the first 4 hours, the accumulated drug release of DOX NP at pH 5.0 and pH 7.4 was approximately 27.1% and 13.3%, respectively. Comparatively, the initial burst release of drug was not observed for the drug-loaded polypeptide-based nanocarriers with protective shell of the present invention (M-DOX NP). In the first 4 hours, the accumulated DOX release of M-DOX NP at pH 5.0 and pH 7.4 was approximately 0% and 5%, respectively, which indicated that the mineralized protective shell of calcium phosphate in M-DOX NP provided protective effect against premature drug release. After 24 hours, the drug-loaded polypeptide-based nanocarriers without protective shell showed fast release of drug at the physiological condition of pH 7.4 with the accumulated drug release being about 39.8%. In contrast, the drug-loaded polypeptide-based nanocarriers with protective shell of the present invention effectively inhibited drug leakage at pH 7.4 with the accumulated drug release being only about 5%. When the environment had an acidic pH, such as pH 5.0, both the drug-loaded polypeptide-based nanocarriers without protective shell and the drug-loaded polypeptide-based nanocarriers with protective shell of the present invention remarkably released the encapsulated drug within 24 hours with the accumulated drug release being about 60.6% and 54.9%, respectively. After 50 hours, the accumulated drug release of the two types of polypeptide-based nanocarriers similarly reached about 70%. These results indicate that the drug-loaded polypeptide-based nanocarrier with protective shell of the present invention not only exhibits high stability and prevents premature drug release at the physiological condition, but also achieves remarkable release of the encapsulated drug at decreasing pH due to its sensitivity to environmental stimuli.

Example 6

Cellular Uptake and Intracellular Drug Release of the Drug-Loaded Polypeptide-Based Nanocarrier with Protective Shell The cellular uptake and the intracellular drug release of the drug-loaded polypeptide-based nanocarrier with protective shell of the present invention in conjunction with or without the active targeting molecule, LyP-1 peptide, were studied in this example using human breast adenocarcinoma cells, MDA-MB-231, and human umbilical vein endothelial cells (HUVEC) as the tumor tissue models. In the beginning, $10^5$ breast adenocarcinoma cells MDA-MB-231 or HUVEC cells were seeded in each well of a 2-well chamber slide with 2 ml medium supplemented with serum. Next, a medium containing the DOX-loaded polypeptide-based nanocarriers with protective shell of calcium phosphate and also with or without LyP-1 peptide at concentrations equivalent to 10 µg/ml DOX were added. The cells were then incubated with the abovementioned nanocarriers at 37° C. for 4 hours. Afterwards, the medium was removed and the cells were rinsed with PBS 3 times. The cells were then fixed with 4% formaldehyde and the nuclei were stained with DAPI, a blue fluorescent DNA dye. The fluorescence micrographs of cells were obtained by an upright fluorescence microscope ZEISS Axio Scope. A1 (Oerkochen, Germany).

Figure 8A:
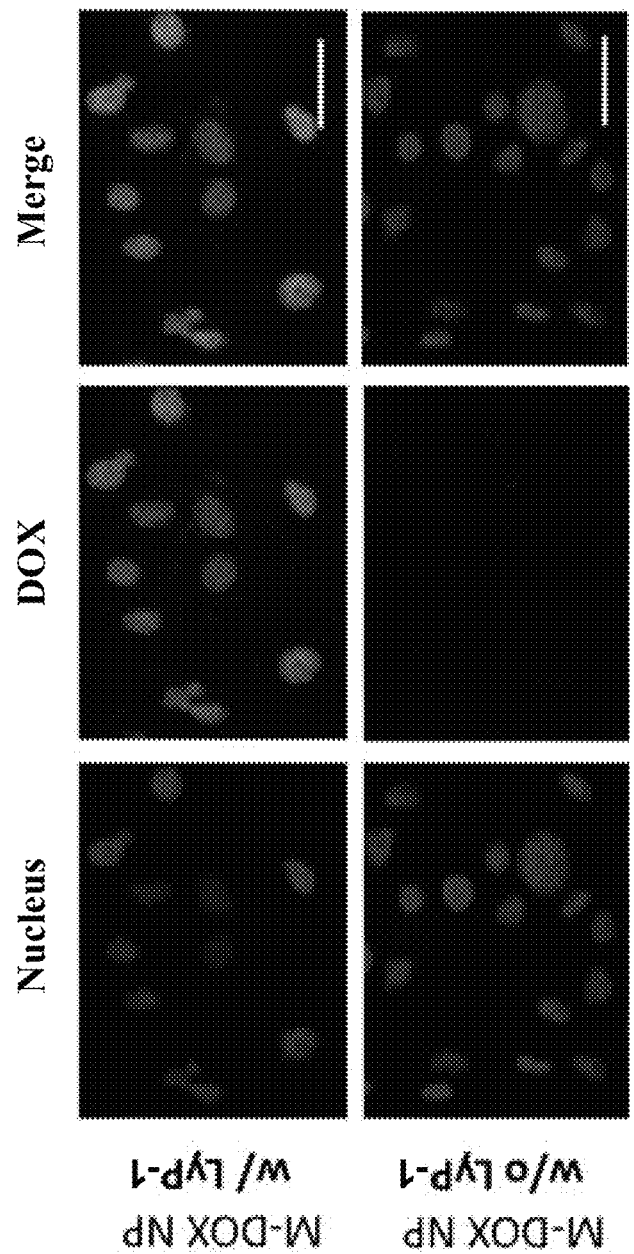
FIG. 8A shows fluorescence micrographs of the human breast adenocarcinoma cells MDA-MB-231 treated for 4 hours with the DOX-loaded polypeptide-based nanocarriers with protective shell of calcium phosphate and with LyP-1 peptide (M-DOX NP w/LyP-1) of the present invention or the DOX-loaded polypeptide-based nanocarriers with protective shell of calcium phosphate and without LyP-1 peptide (M-DOX NP w/o LyP-1); the scale bar in the figure represents 50 µm.

As shown in FIG. 8A, after 4-hour co-incubation of the breast adenocarcinoma cells MDA-MB-231 with the drug-loaded polypeptide-based nanocarriers with protective shell and with LyP-1 peptide (M-DOX NP w/LyP-1) of the present invention, fast accumulation of the released drug (DOX) in nuclei of the breast adenocarcinoma cells was observed, and the result was confirmed by the overlapping fluorescence signal of DAPI in nuclei and the drug. However, when the breast adenocarcinoma cells were co-incubated with the drug-loaded polypeptide-based nanocarriers with protective shell and without LyP-1 peptide (M-DOX NP w/o LyP-1), the fluorescence of the released drug mainly located in the perinuclei region with low intensity. The results indicate that the active targeting molecule, LyP-1 peptide, causes efficient engulfment of the drug-loaded polypeptide-based nanocarrier with protective shell of the present invention by the breast adenocarcinoma cells MDA-MB-231 via receptor-mediated endocytosis, leading to drug release into the target cells and the following nuclear transport.

Figure 8B:
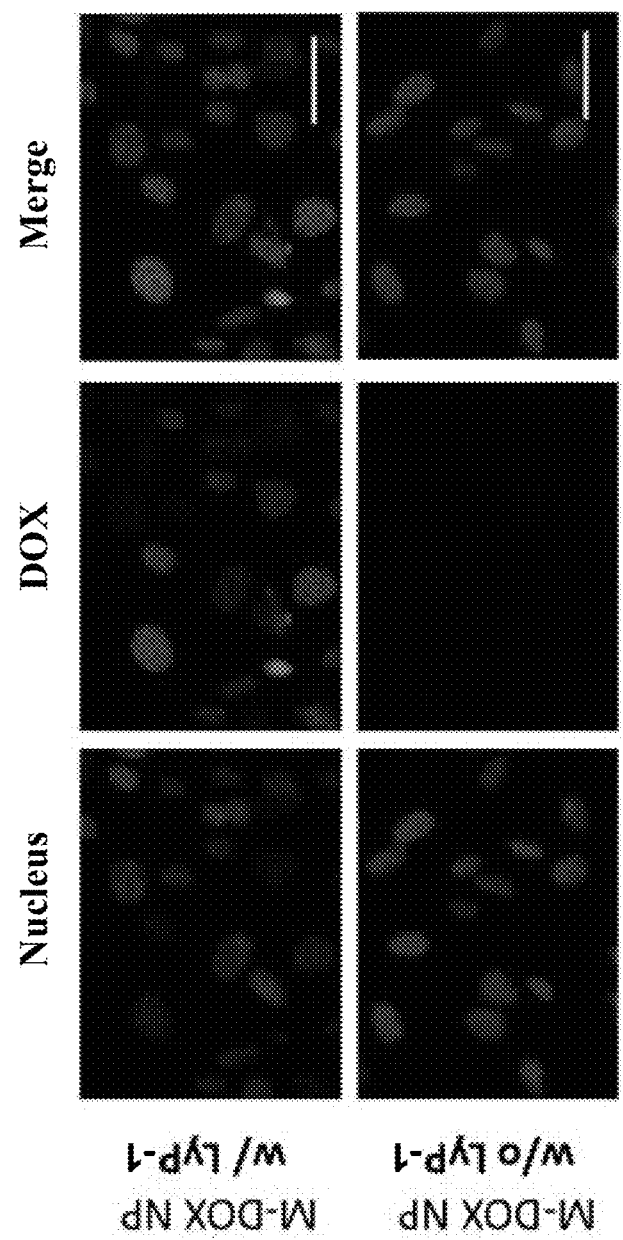
FIG. 8B shows fluorescence micrographs of the activated human umbilical vein endothelial cells treated for 4 hours with the DOX-loaded polypeptide-based nanocarriers with protective shell of calcium phosphate and with LyP-1 peptide (M-DOX NP w/LyP-1) of the present invention or the DOX-loaded polypeptide-based nanocarriers with protective shell of calcium phosphate and without LyP-1 peptide (M-DOX NP w/o LyP-1); the scale bar in the figure represents 50 µm.

Moreover, as shown in FIG. 8B, after 4-hour co-incubation of the activated human umbilical vein endothelial cells with the drug-loaded polypeptide-based nanocarriers with protective shell and with LyP-1 peptide (M-DOX NP w/LyP-1), accumulation of the released drug in nuclei of the endothelial cells was observed, though the amount of this accumulation was less than that in the breast adenocarcinoma cells previous described. Compared with cell treatment with the drug-loaded polypeptide-based nanocarriers with protective shell and without LyP-1 peptide (M-DOX NP w/o LyP-1), the drug-loaded polypeptide-based nanocarriers with protective shell and with LyP-1 peptide of the present invention resulted in significantly more drug accumulation in nuclei of the endothelial cells. This result once again proves that the active targeting molecule, such as LyP-1 peptide, efficiently directs the drug-loaded polypeptide-based nanocarrier with protective shell of the present invention to the target cells for drug release. This result also indicates that p32, the receptor for LyP-1 peptide, is expressed on the surface of the angiogenic endothelial cells. Thus, when using the LyP-1 peptide as an active targeting molecule, the drug-loaded polypeptide-based nanocarrier with protective shell of the present invention has the potential to inhibit metastasis of the breast adenocarcinoma cells MDA-MB-231 through targeting the angiogenic blood vessels.

Example 7

Anti-Tumor Activity of the Drug-Loaded Polypeptide-Based Nanocarrier with Protective Shell The anti-tumor activity of the drug-loaded polypeptide-based nanocarrier with protective shell of the present invention was evaluated in this example by cell viability assay (MTS assay) on human breast adenocarcinoma cells MDA-MB-231 cells. The cells were seeded in a 96-well plate ($5 \times 10^3$ cells/well) and cultured in L-15 medium supplemented with 10% FBS and 1% penicillin and streptomycin at 37° C. for 1 day. Next, the medium was removed, and cells were treated with 100 µl L-15 medium containing DOX.HCl, the DOX-loaded polypeptide-based nanocarriers with protective shell of calcium phosphate and with LyP-1 peptide (M-DOX NP w/LyP-1), or the DOX-loaded polypeptide-based nanocarriers with protective shell of calcium phosphate and without LyP-1 peptide (M-DOX NP w/o LyP-1) at concentrations equivalent to 10 µg/ml DOX for 24 hours. The cells were rinsed with PBS 2 times and incubated with L-15 medium supplemented with 10% FBS and 1% penicillin and streptomycin at 37° C. for 24 hours, 48 hours, or 72 hours. To carry out the cell viability assay, the medium was first discarded from the 96-well plate, 10 µl MTS solution and 90 μl L-15 medium were added for incubation at 37° C. for 2.5 hours, and the solution was transferred to a new 96-well plate for measurement of light absorption at 490 nm. The assay was repeated 3 times.

Figure 9:
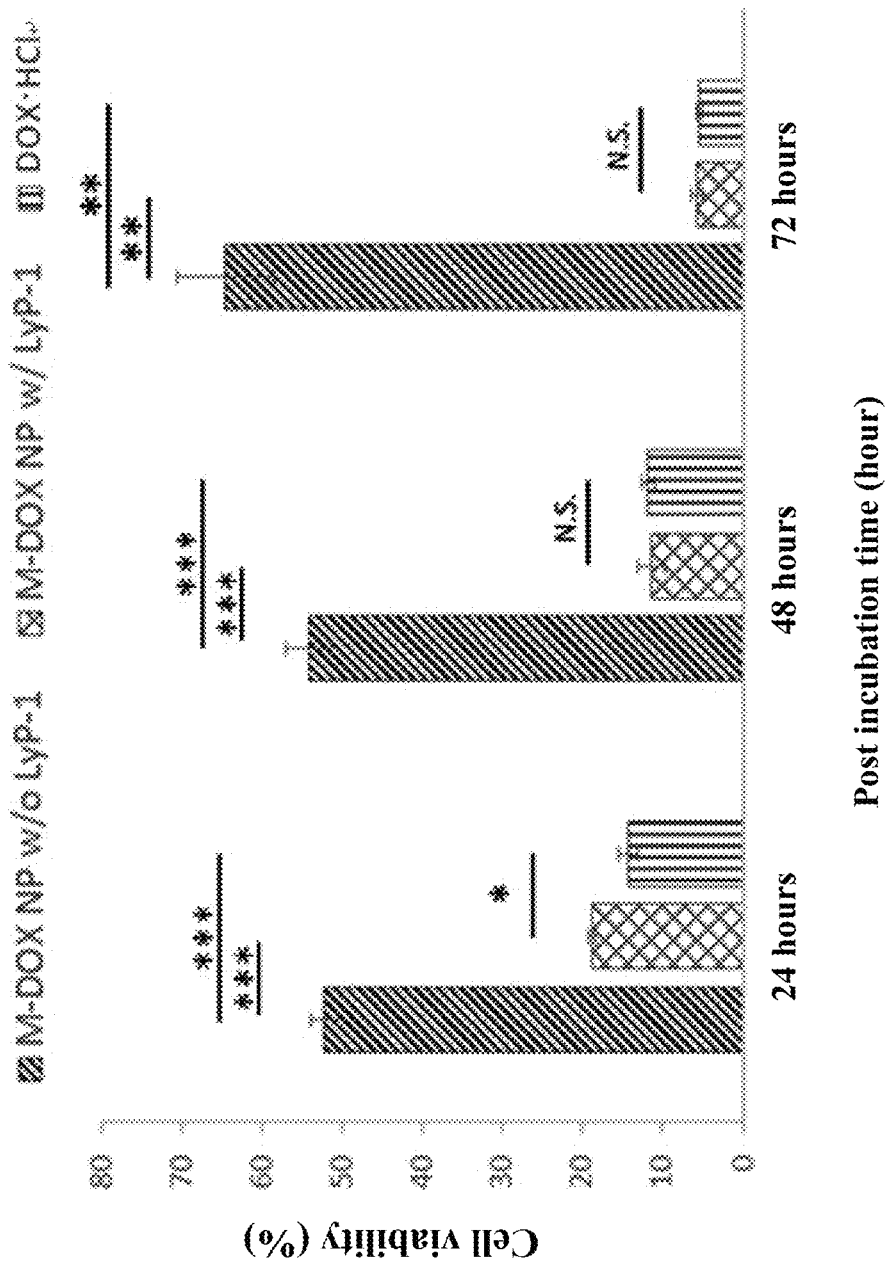
FIG. 9 shows cell viability of the human breast adenocarcinoma cells MDA-MB-231 treated for 24 hours with DOX.HCl or the DOX-loaded polypeptide-based nanocarriers with protective shell of calcium phosphate and with LyP-1 peptide (M-DOX NP w/LyP-1) of the present invention or the DOX-loaded polypeptide-based nanocarriers with protective shell of calcium phosphate and without LyP-1 peptide (M-DOX NP w/o LyP-1)

As shown in FIG. 9, after treatment with the drug-loaded polypeptide-based nanocarriers with protective shell and without LyP-1 peptide, the viability of the breast adenocarcinoma cells decreased to 52.3%, indicating that the nanocarriers were engulfed by the breast adenocarcinoma cells through phagocytosis. In contrast, after treatment with the drug-loaded polypeptide-based nanocarriers with protective shell and with LyP-1 peptide, the viability of the breast adenocarcinoma cells decreased substantially to 18.8%, which was comparable to that of the breast adenocarcinoma cells treated directly with the drug (14.3%). When the cells were kept incubated for 72 hours, the drug-loaded polypeptide-based nanocarriers with protective shell of the present invention maintained the anti-tumor activity and caused a decrease of viability of the breast adenocarcinoma cells to 5.7% with time, which showed a similar trend that the viability of the breast adenocarcinoma cells decreased with time to 5.4% after direct drug treatment. The results indicate that the active targeting molecule, LyP-1 peptide, efficiently promotes the cellular uptake of the drug-loaded polypeptide-based nanocarrier with protective shell of the present invention by the breast adenocarcinoma cells MDA-MB-231 via receptor-mediated endocytosis, leading to significant inhibition of tumor cell viability. In FIG. 9, * indicates $p<0.05$,  indicates $p<0.01$, * indicates $p<0.001$, and N.S. indicates no significant difference.

Example 8

Inhibitory Effect of the Drug-Loaded Polypeptide-Based Nanocarrier with Protective Shell on Metastatic Invasion The inhibitory effect of the drug-loaded polypeptide-based nanocarrier with protective shell of the present invention on metastatic invasion was evaluated in this example using the metastatic human breast adenocarcinoma cells MDA-MB-231 as the in vitro metastatic model. The drug-loaded polypeptide-based nanocarrier with protective shell in this example had a mineralized protective shell of calcium phosphate and encapsulated two drugs suppressing metastasis of cancer cells. One of the drugs was latrunculin B, which inhibited actin filament organization; the other was GM6001, an inhibitor reducing protein expression levels of matrix metalloproteinases. During the experiment, $10^5$ breast adenocarcinoma cells were first incubated in Matrigel containing L-15 medium in each well of an 8-well chamber slide. The L-15 medium was mixed with the Matrigel in a ratio of 2:3. The cells of the experimental group were treated with the drug-loaded polypeptide-based nanocarriers with protective shell of the present invention at 1 mg/ml while the cells of the control group were not. After gelation for 10 minutes, a hole with a diameter of 5 mm was made in the Matrigel, and the circular vacancy was washed with PBS twice. The circular vacancy was then filled with Matrigel mixed with epidermal growth factor (EGF) and C—X—C motif chemokine 12 (CXCL12), both of which were paracrine factors promoting metastasis, to form a circular inner Matrigel. After cell incubation for 1 day, 3 days, and 6 days, invasion of the breast adenocarcinoma cells which was stained with the green fluorescent dye CMFDA into the circular inner Matrigel was monitored by confocal laser scanning microscope ZEISS LSM 700 (Oerkochen, Germany).

Figure 10:
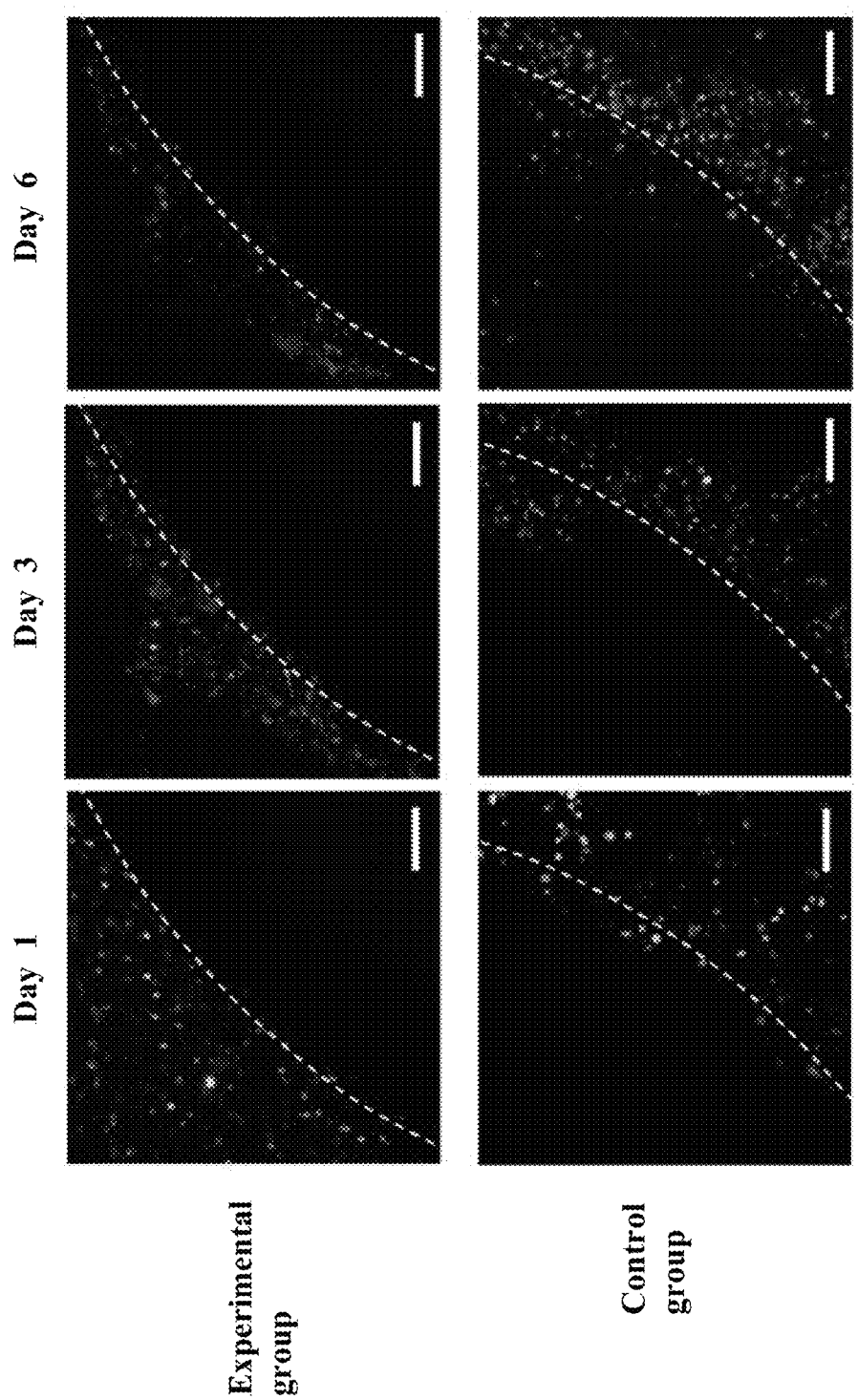
FIG. 10 shows fluorescence micrographs of the inhibited cell invasion of the human breast adenocarcinoma cells MDA-MB-231 after treatment with the latrunculin B and GM6001-loaded polypeptide-based nanocarriers with protective shell of calcium phosphate of the present invention; the dashed line indicates the boundary line between the initial distribution area of the breast adenocarcinoma cells and the region invaded by the cells, and the scale bar represents 200 µm in the figure.

FIG. 10 are fluorescence micrographs recording the invasion of the breast adenocarcinoma cells, with the dashed line indicating the boundary line between the initial distribution area of the breast adenocarcinoma cells and the circular inner Matrigel into which the cells invaded. The breast adenocarcinoma cells of the control group exhibited strong tendency to migrate into the circular inner Matrigel containing EGF and CXCL12. Particularly, the migration distances of these breast adenocarcinoma cells were up to several hundred micrometers (μm) after incubation for 6 days, indicating chemotaxis of the breast adenocarcinoma cells. On the contrary, the invasive ability of the breast adenocarcinoma cells of the experimental group was significantly restrained due to the drug-loaded polypeptide-based nanocarriers with protective shell, leading to limited cell migration mainly to the junction of the Matrigel where the cells were at the beginning and the circular inner Matrigel containing EGF and CXCL12. The migration distances of these breast adenocarcinoma cells were less than 100 μm. The results indicate that the drug-loaded polypeptide-based nanocarrier with protective shell of the present invention is able to be taken up by the breast adenocarcinoma cells MDA-MB-231 and release drugs intracellularly, and thus effectively suppresses metastatic invasion of tumor cells.

In conclusion, the sequentially decomposable polypeptide-based nanocarrier with protective shell of the present invention is prepared from biocompatible and biodegradable materials, such as polyethylene glycol, polypeptide, calcium phosphate, and LyP-1. Thus, it is considered highly safe for administration in the body. The drug-loaded polypeptide-based nanocarrier with protective shell, which is formed from the polypeptide-based nanocarrier with protective shell of the present invention, has shown high stability in aqueous solutions, high drug loading efficiency, multi-pH responsiveness or even redox responsiveness, and efficient cellular uptake and intracellular drug release. It progressively collapses upon changes in environmental pH or redox status. It has also exhibited significant anti-tumor activity and an inhibitory effect on metastatic invasion in cancer cell experiments. Therefore, the sequentially decomposable polypeptide-based nanocarrier with protective shell of the present invention may be exploited as a platform for delivery of hydrophobic drugs. For example, it is used to prepare a pharmaceutical composition to inhibit tumors and metastasis by encapsulating anti-cancer drugs or to track distribution of tumors in the body by encapsulating iodine imaging agents. Due to the abovementioned characteristics, the pharmaceutical composition can stably encapsulate drugs and prevent drug leakage or premature drug release before reaching the target tissue while it is administered to the body, and it can also decompose progressively in response to a decrease of the environmental pH and release drugs completely in the target cells while it arrives at the target tissue such as tumor tissue.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A sequentially decomposable polypeptide-based nanocarrier with a protective shell, comprising:
a plurality of first polypeptide-based copolymers, each comprising a first hydrophilic polymer and a first polypeptide, wherein the first hydrophilic polymer is conjugated to the N-terminus of the first polypeptide via an acid-labile linkage; and
a plurality of second polypeptide-based copolymers, each comprising a second hydrophilic polymer, a second polypeptide, and an active targeting molecule, wherein the second hydrophilic polymer is conjugated at one end to the N-terminus of the second polypeptide and conjugated at the other end to the active targeting molecule;
wherein the plurality of first polypeptide-based copolymers and the plurality of second polypeptide-based copolymers are assembled into a polypeptide core and a hydrophilic polymer outer layer;
wherein the first polypeptide-based copolymers and the second polypeptide-based copolymers are mixed and aligned radially in the polypeptide-based nanocarrier with the protective shell;
wherein the first hydrophilic polymer has a molecular weight of 3400 Da, and the second hydrophilic polymer has a molecular weight of 1100 Da;
wherein both the first polypeptide and the second polypeptide have a first amino acid sequence, and each sequentially comprises an acidic amino acid segment, an acid-responsive amino acid segment, and a hydrophobic amino acid segment from the N-terminus to the C-terminus;
wherein the acid-responsive amino acid segment consists of an amino acid having a side chain with a pKa value of about 6; and
wherein the protective shell is an acid-soluble mineralized protective shell comprising an acid-soluble mineral deposited on the acidic amino acid segment.

2. The polypeptide-based nanocarrier with the protective shell of claim 1, wherein the first polypeptide-based copolymers and the second polypeptide-based copolymers are in a molar ratio of about 1:2 to 2:1, and the polypeptide-based nanocarrier with the protective shell is at a size of about 100-200 nm.

3. The polypeptide-based nanocarrier with the protective shell of claim 1, wherein the acidic amino acid segment consists of 10-20 acidic amino acid residues, the acid-responsive amino acid segment consists of 5-15 acid-responsive amino acid residues, and the hydrophobic amino acid segment consists of 5-15 hydrophobic amino acid residues.

4. The polypeptide-based nanocarrier with the protective shell of claim 1, wherein the acidic amino acid segment consists of glutamic acid, aspartic acid, or combinations thereof.

5. The polypeptide-based nanocarrier with the protective shell of claim 1, wherein the acid-labile linkage is hydrolyzed at pH 6.5-7.

6. The polypeptide-based nanocarrier with the protective shell of claim 1, wherein the acid-soluble mineral is calcium phosphate or calcium carbonate.

7. The polypeptide-based nanocarrier with the protective shell of claim 1, which further encapsulates a hydrophobic agent.

8. A sequentially decomposable polypeptide-based nanocarrier with a protective shell, comprising:
a plurality of first polypeptide-based copolymers, each comprising a first hydrophilic polymer and a first polypeptide, wherein the first hydrophilic polymer is conjugated to the N-terminus of the first polypeptide via an acid-labile linkage; and a plurality of second polypeptide-based copolymers, each comprising a second hydrophilic polymer, a second polypeptide, and an active targeting molecule, wherein the second hydrophilic polymer is conjugated at one end to the N-terminus of the second polypeptide and conjugated at the other end to the active targeting molecule;

wherein the plurality of first polypeptide-based copolymers and the plurality of second polypeptide-based copolymers are assembled into a polypeptide core and a hydrophilic polymer outer layer;

wherein the first polypeptide-based copolymers and the second polypeptide-based copolymers are mixed and aligned radially in the polypeptide-based nanocarrier with protective shell;

wherein the first hydrophilic polymer has a molecular weight of 3400 Da, and the second hydrophilic polymer has a molecular weight of 1100 Da;

wherein both the first polypeptide and the second polypeptide have a first amino acid sequence, and each sequentially comprises a cysteine segment, an acid-responsive amino acid segment, and a hydrophobic amino acid segment from the N-terminus to the C-terminus; wherein the acid-responsive amino acid segment consists of an amino acid having a side chain with a pKa value of about 6; and wherein the protective shell is a redox-responsive protective shell comprising a plurality of disulfide bonds between the cysteine segments of the first polypeptide-based copolymers and the second polypeptide-based copolymers in proximity to each other.

9. The polypeptide-based nanocarrier with the protective shell of claim 8, wherein the first polypeptide-based copolymers and the second polypeptide-based-copolymers are in a molar ratio of about 1:2 to 2:1, and the polypeptide-based nanocarrier with the protective shell is at a size of about 100-200 nm.

10. The polypeptide-based nanocarrier with the protective shell of claim 8, wherein the acid-labile linkage is hydrolyzed at pH 6.5-7.

11. The polypeptide-based nanocarrier with the protective shell of claim 8, which further encapsulates a hydrophobic agent.

12. A method of preparing the sequentially decomposable polypeptide-based nanocarrier with the protective shell of claim 1, comprising the steps of:

(a) preparing separately a first polypeptide-based copolymer and a second polypeptide-based copolymer by chemical grafting, wherein the first polypeptide-based copolymer comprises a first hydrophilic polymer and a first polypeptide, and the second polypeptide-based copolymer comprises a second hydrophilic polymer and a second polypeptide, wherein both the first polypeptide and the second polypeptide have a first amino acid sequence, and each sequentially comprises an acidic amino acid segment, an acid-responsive amino acid segment, and a hydrophobic amino acid segment from the N-terminus to the C-terminus, wherein the first hydrophilic polymer and the acidic amino acid segment of the first polypeptide are conjugated by an acid-labile linkage, and an end of the second hydrophilic polymer is conjugated with an active targeting molecule, wherein the first hydrophilic polymer is conjugated to the N-terminus of the first polypeptide via the acid-labile linkage, and the second hydrophilic polymer is conjugated at one end to the N-terminus of the second polypeptide and conjugated at the other end to the active targeting molecule; wherein the first hydrophilic polymer has a molecular weight of 3400 Da, and the second hydrophilic polymer has a molecular weight of 1100 Da;

(b) mixing the first polypeptide-based copolymer and the second polypeptide-based copolymer in a polar solvent to allow self-assembly into a polypeptide-based nanocarrier; and (c) adding a cation aqueous solution and an anion aqueous solution into the polar solvent containing the polypeptide-based nanocarrier to form a first layer of an acid-soluble mineralized protective shell on the acidic amino acid segment of the polypeptide-based nanocarrier, and repeating the addition step multiple times for formation of multiple layers of the acid-soluble mineralized protective shell to obtain the polypeptide-based nanocarrier with the protective shell.

13. The method of claim 12, wherein in step (c) the cation aqueous solution is a calcium ion aqueous solution, the anion aqueous solution is a phosphate aqueous solution or a carbonate aqueous solution, and the addition step is repeated at least 5 times.

14. The method of claim 12, wherein in step (b) the first polypeptide-based-copolymer and the second polypeptide-based copolymer are mixed in a molar ratio of about 1:2 to 2:1.

15. The method of claim 12, wherein in step (a) the acidic amino acid segment consists of 10-20 acidic amino acid residues, the acid-responsive amino acid segment consists of 5-15 acid-responsive amino acid residues, and the hydrophobic amino acid segment consists of 5-15 hydrophobic amino acid residues.

16. The method of claim 12, wherein in step (a) the acidic amino acid segment consists of glutamic acid, aspartic acid, or combinations thereof.

17. The method of claim 12, wherein in step (a) the acid-labile linkage is hydrolyzed at pH 6.5-7.

* * * * *

SEQUENCE LISTING

```
<160> NUMBER OF SEQ ID NOS: 2

<210> SEQ ID NO 1
<211> LENGTH: 35
<212> TYPE: PRT
<213> ORGANISM: Artificial sequence
<220> FEATURE:
<223> OTHER INFORMATION: polypeptide E15-H10-L10

<400> SEQUENCE: 1

Glu Glu Glu Glu Glu Glu Glu Glu Glu Glu Glu Glu Glu Glu Glu His
1               5                   10                  15

His His His His His His His His His Leu Leu Leu Leu Leu Leu Leu
            20                  25                  30

Leu Leu Leu
        35

<210> SEQ ID NO 2
<211> LENGTH: 9
<212> TYPE: PRT
<213> ORGANISM: Artificial Sequence
<220> FEATURE:
<223> OTHER INFORMATION: LyP-1 peptide

<400> SEQUENCE: 2

Cys Gly Asn Lys Arg Thr Arg Gly Cys
1               5
```